(12) United States Patent
Grabowski et al.

(10) Patent No.: US 10,864,255 B2
(45) Date of Patent: Dec. 15, 2020

(54) LIPID HYDROLYSIS THERAPY FOR ATHEROSCLEROSIS AND RELATED DISEASES

(71) Applicant: Children's Hospital Medical Center, Cincinnati, OH (US)

(72) Inventors: Gregory A. Grabowski, Wheat Ridge, CO (US); Hong Du, Carmel, IN (US)

(73) Assignee: Children's Hospital Medical Center, Cincinnati, OH (US)

( * ) Notice: Subject to any disclaimer, the term of this patent is extended or adjusted under 35 U.S.C. 154(b) by 232 days.

(21) Appl. No.: 15/430,815

(22) Filed: Feb. 13, 2017

(65) Prior Publication Data

US 2017/0151313 A1    Jun. 1, 2017

Related U.S. Application Data

(60) Continuation of application No. 12/683,265, filed on Jan. 6, 2010, now abandoned, which is a continuation of application No. 10/776,797, filed on Feb. 11, 2004, now abandoned, which is a division of application No. 09/775,517, filed on Feb. 2, 2001, now Pat. No. 6,849,257.

(60) Provisional application No. 60/180,362, filed on Feb. 4, 2000.

(51) Int. Cl.
| | |
|---|---|
| *C12N 9/20* | (2006.01) |
| *A61K 38/46* | (2006.01) |
| *A23L 33/18* | (2016.01) |
| *A61K 48/00* | (2006.01) |
| *C12N 7/00* | (2006.01) |
| *A61K 9/00* | (2006.01) |
| *A61K 38/18* | (2006.01) |
| *A61K 38/40* | (2006.01) |

(52) U.S. Cl.
CPC ............ *A61K 38/465* (2013.01); *A23L 33/18* (2016.08); *A61K 9/0019* (2013.01); *A61K 48/005* (2013.01); *C12N 7/00* (2013.01); *C12N 9/20* (2013.01); *C12Y 301/01013* (2013.01); *A61K 38/18* (2013.01); *A61K 38/40* (2013.01); *A61K 48/00* (2013.01); *C12N 2799/021* (2013.01); *C12N 2799/04* (2013.01)

(58) Field of Classification Search
CPC .................................................... A61K 38/465
USPC ........................................................ 435/199
See application file for complete search history.

(56) References Cited

U.S. PATENT DOCUMENTS

| | | |
|---|---|---|
| 3,710,795 A | 1/1973 | Higuchi et al. |
| 4,105,776 A | 8/1978 | Ondetti et al. |
| 4,231,938 A | 11/1980 | Monaghan et al. |
| 4,302,386 A | 11/1981 | Stevens |
| 4,316,906 A | 2/1982 | Ondetti et al. |
| 4,337,201 A | 6/1982 | Petrillo, Jr. |
| 4,344,949 A | 8/1982 | Hoefle et al. |
| 4,346,227 A | 8/1982 | Terahara et al. |
| 4,374,829 A | 2/1983 | Harris |
| 4,410,520 A | 10/1983 | Watthey |
| 4,444,784 A | 4/1984 | Hoffman et al. |
| 4,508,729 A | 4/1985 | Vincent et al. |
| 4,512,912 A | 4/1985 | Matsuda et al. |
| 4,587,258 A | 5/1986 | Gold et al. |
| 4,739,073 A | 4/1988 | Kathawala |
| 4,772,684 A | 9/1988 | Brunck et al. |
| 4,816,463 A | 3/1989 | Blankley et al. |
| 4,897,402 A | 1/1990 | Duggan et al. |
| 4,906,624 A | 3/1990 | Chucholowski et al. |
| 4,906,657 A | 3/1990 | Roth |
| 4,920,109 A | 4/1990 | Onishi et al. |
| 4,923,861 A | 5/1990 | Picard et al. |
| 4,929,620 A | 5/1990 | Chuckolowski et al. |
| 4,939,143 A | 7/1990 | Regan et al. |
| 4,940,727 A | 7/1990 | Inamine et al. |
| 4,940,800 A | 7/1990 | Bertolini et al. |
| 4,946,860 A | 8/1990 | Morris et al. |
| 4,946,864 A | 8/1990 | Prugh et al. |
| 4,950,675 A | 8/1990 | Chucholowski |
| 4,957,940 A | 9/1990 | Roth |
| 4,962,885 A | 10/1990 | Coffee |
| 4,963,538 A | 10/1990 | Duggan et al. |
| 4,968,693 A | 11/1990 | Joshua et al. |

(Continued)

FOREIGN PATENT DOCUMENTS

| | | |
|---|---|---|
| BR | PI0108077 A | 10/2002 |
| EP | 0 253 310 | 1/1988 |

(Continued)

OTHER PUBLICATIONS

Anderson, R. A., and Sando, G. N. 1991, J. Biol. Chem., vol. 266, pp. 22479-22484.*

Abramov, et al., "Generalized Xanthomatosis with Calcified Adrenals," Journal of Diseases of Children, pp. 282-250 (1956).

Achord, D., et al., "Human β-Glucuronidase. II. Fate of Infused Human Placental β-Glucuronidase in the Rat," Pediat. Res., 1977, vol. 11, pp. 816-822.

(Continued)

*Primary Examiner* — Tekchand Saidha
(74) *Attorney, Agent, or Firm* — Frost Brown Todd LLC; Nicole M. Tepe

(57) ABSTRACT

The present invention comprises a method to diminish and/or eliminate atherosclerotic plaques, in mammals, through direct and indirect treatment of these plaques, in situ, using suitable substances which are capable of lipid removal, primarily through hydrolysis, either by a catalytic or stoichiometric process, wherein the substance targets receptors in and/or on the cell which lead to uptake into the lysosome. Such substances used to diminish and/or eliminate atherosclerotic plaques are generally comprised of lipid hydrolyzing proteins and/or polypeptides.

3 Claims, 4 Drawing Sheets

(56) References Cited

U.S. PATENT DOCUMENTS

| | | |
|---|---|---|
| 4,970,231 A | 11/1990 | Lee et al. |
| 4,992,429 A | 2/1991 | Ullrich et al. |
| 4,994,494 A | 2/1991 | Regan et al. |
| 4,996,234 A | 2/1991 | Regan et al. |
| 4,997,837 A | 3/1991 | Chucholowski et al. |
| 5,001,128 A | 3/1991 | Neuenschwander et al. |
| 5,001,144 A | 3/1991 | Regan et al. |
| 5,017,716 A | 5/1991 | Karanewsky et al. |
| 5,021,453 A | 6/1991 | Joshua et al. |
| 5,025,000 A | 6/1991 | Karanewsky |
| 5,064,825 A | 11/1991 | Chakravarty et al. |
| 5,073,566 A | 12/1991 | Lifer et al. |
| 5,081,127 A | 1/1992 | Carini et al. |
| 5,081,136 A | 1/1992 | Bertolini et al. |
| 5,085,992 A | 2/1992 | Chen et al. |
| 5,087,634 A | 2/1992 | Reitz et al. |
| 5,091,378 A | 2/1992 | Karanewsky et al. |
| 5,091,386 A | 2/1992 | Kesseler et al. |
| 5,098,931 A | 3/1992 | Duggan et al. |
| 5,102,911 A | 4/1992 | Lee et al. |
| 5,112,857 A | 5/1992 | Vickers |
| 5,116,870 A | 5/1992 | Smith et al. |
| 5,130,306 A | 7/1992 | Duggan et al. |
| 5,132,312 A | 7/1992 | Regan et al. |
| 5,135,935 A | 8/1992 | Alberts et al. |
| 5,166,171 A | 11/1992 | Jendralla et al. |
| 5,182,298 A | 1/1993 | Helms et al. |
| 5,196,440 A | 3/1993 | Bertolini et al. |
| 5,202,327 A | 4/1993 | Robl |
| 5,250,435 A | 10/1993 | Cover et al. |
| 5,256,689 A | 10/1993 | Chiang |
| 5,260,332 A | 11/1993 | Dufresne |
| 5,262,435 A | 11/1993 | Joshua et al. |
| 5,273,995 A | 12/1993 | Roth |
| 5,276,021 A | 1/1994 | Karanewsky et al. |
| 5,279,940 A | 1/1994 | Kissel |
| 5,283,256 A | 2/1994 | Dufresne et al. |
| 5,286,895 A | 2/1994 | Harris et al. |
| 5,302,604 A | 4/1994 | Byrne et al. |
| 5,317,031 A | 5/1994 | MacConnell |
| 5,356,896 A | 10/1994 | Kabadi et al. |
| 5,369,125 A | 11/1994 | Berger et al. |
| 5,385,932 A | 1/1995 | Vickers |
| 5,440,020 A | 8/1995 | Coller |
| 5,474,995 A | 12/1995 | Ducharme et al. |
| 5,543,297 A | 8/1996 | Cromlish et al. |
| 5,622,985 A | 4/1997 | Olukotun et al. |
| 5,813,614 A | 9/1998 | Coffee |
| 5,873,523 A | 2/1999 | Gomez et al. |
| 5,900,360 A | 5/1999 | Welch et al. |
| 5,904,646 A | 5/1999 | Jarvik |
| 5,915,377 A | 6/1999 | Coffee |
| 5,929,304 A | 7/1999 | Radin et al. |
| 6,103,271 A | 8/2000 | Morrison et al. |
| 6,105,571 A | 8/2000 | Coffee |
| 6,105,877 A | 8/2000 | Coffee |
| 6,136,804 A | 10/2000 | Nichtberger |
| 6,270,954 B1 | 8/2001 | Welch et al. |
| 6,319,716 B1 | 11/2001 | Tikoo |
| 6,458,819 B1 | 10/2002 | Wagle et al. |
| 6,471,943 B1 | 10/2002 | Placke et al. |
| 6,503,481 B1 | 1/2003 | Thurston et al. |
| 6,528,315 B2 | 3/2003 | Bureau et al. |
| 6,534,300 B1 | 3/2003 | Canfield |
| 6,541,195 B2 | 4/2003 | Welch et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,670,165 B2 | 12/2003 | Canfield |
| 6,800,472 B2 | 10/2004 | Canfield et al. |
| 6,849,257 B2 * | 2/2005 | Grabowski ............ C12N 9/20 424/94.6 |
| 6,861,053 B1 | 3/2005 | Lin et al. |
| 6,913,761 B1 | 7/2005 | Trigg et al. |
| 7,008,934 B2 | 3/2006 | Yu |
| 7,122,201 B2 | 10/2006 | Yu et al. |
| 7,335,512 B2 | 2/2008 | Callewaert et al. |
| 7,655,226 B2 | 2/2010 | Van Bree et al. |
| 7,910,545 B2 | 3/2011 | Meeker et al. |
| 7,927,587 B2 | 4/2011 | Blazar et al. |
| 8,143,265 B2 | 3/2012 | ZhongMao |
| 8,178,609 B2 | 5/2012 | Grynkiewicz et al. |
| 8,183,003 B2 | 5/2012 | Crawford et al. |
| 8,232,073 B2 | 7/2012 | Crawford et al. |
| 8,466,118 B2 | 6/2013 | Banks et al. |
| 8,604,057 B2 | 12/2013 | Boyd et al. |
| 8,609,065 B2 | 12/2013 | Kuik-Romeijn et al. |
| 8,623,910 B2 | 1/2014 | Grynkiewicz et al. |
| 8,663,631 B2 | 3/2014 | Quinn |
| 8,722,862 B2 | 5/2014 | Rossomando et al. |
| 8,729,029 B2 | 5/2014 | Khrestchatisky et al. |
| 8,748,567 B2 | 6/2014 | Narasimhaswamy et al. |
| 8,865,881 B2 | 10/2014 | Balazes et al. |
| 8,900,551 B2 | 12/2014 | Lee et al. |
| 8,956,825 B2 | 2/2015 | Weisbart |
| 2002/0193303 A1 | 12/2002 | Kapeller-Libermann |
| 2003/0064467 A1 | 4/2003 | Baker et al. |
| 2004/0038365 A1 | 2/2004 | Xiao |
| 2004/0175798 A1 | 9/2004 | Wan et al. |
| 2004/0223960 A1 | 11/2004 | Grabowski et al. |
| 2005/0181474 A1 | 8/2005 | Giordano et al. |
| 2007/0264249 A1 | 11/2007 | Grabowski et al. |
| 2007/0270367 A1 | 11/2007 | Testa et al. |
| 2008/0025958 A1 | 1/2008 | Hannon et al. |
| 2009/0297496 A1 | 12/2009 | Grabowski |
| 2010/0160253 A1 | 6/2010 | Coombe et al. |
| 2010/0239558 A1 | 9/2010 | Grabowski et al. |
| 2010/0291060 A1 | 11/2010 | Sturk et al. |

FOREIGN PATENT DOCUMENTS

| | | |
|---|---|---|
| EP | 1 267 914 | 1/2003 |
| WO | WO 89/07603 | 8/1989 |
| WO | WO 92/16212 | 1/1992 |
| WO | WO 95/00501 | 1/1995 |
| WO | WO 95/18799 | 7/1995 |
| WO | WO 96/04001 | 2/1996 |
| WO | WO 96/41645 | 12/1996 |
| WO | WO 97/05771 | 2/1997 |
| WO | WO 98/11206 | 3/1998 |
| WO | WO 99/20110 | 4/1999 |
| WO | WO 00/09153 | 2/2000 |
| WO | WO 00/77239 | 12/2000 |
| WO | WO 01/56596 | 8/2001 |
| WO | WO 01/97829 | 12/2001 |
| WO | WO 02/36754 | 5/2002 |
| WO | WO 2005/123117 | 12/2005 |
| WO | WO 2007/030375 | 3/2007 |
| WO | WO 2007/137303 | 11/2007 |
| WO | WO 2011/133960 A2 | 10/2011 |
| WO | WO 2012/112677 | 8/2012 |
| WO | WO 2012/159052 | 11/2012 |
| WO | WO 2012/162807 | 12/2012 |
| WO | WO 2012/177639 | 12/2012 |
| WO | WO 2012/177778 | 12/2012 |
| WO | WO 2013/020064 | 2/2013 |

OTHER PUBLICATIONS

Achord, et al., "Human β-Glucuronidase: In Vivo Clearance and in Vitro uptake by a Glycoprotein Recognition System on Reticuloendothelial Cells," Cell, 15:269-278 (1978).

Ahn, J.H. et al., "Identifcation of the genes differentially expressed in human dendritic cell subsets by cDNA subtraction and microarray analysis," Blood, 2002, vol. 100, pp. 1742-1754.

Akcoren, et al, "Cholesteryl Ester Storage Disease: Case Report During Childhood," Pediatric and Developmental Pathology, 2;574-576 (1999).

Al Essa, et al., "Wolman Disease: A Review," Curr Paed Res, 3(1):1-12 (1999).

Altmann, et al., "Insect cells as hosts for the expression of recombinant glycoproteins," Glycoconjugate Journal 16(2), 1999, pp. 109-123.

(56) References Cited

OTHER PUBLICATIONS

Ameis et al., "Lysosomal acid lipase: A pivotal enzyme in the pathogenesis of cholesteryl ester storage disease and Wolman disease," Z Gastroenterol (Suppl. 3) 34:66-67 (1996).
Ameis, D. et al., "A 5' splice-region mutation and a dinucleotide deletion in the lysosomal acid lipase gene in two patients with cholesteryl ester storage disease," Journal of Lipid Research, 1995, vol. 36, pp. 241-250.
Amies, D. et al., "Purification, characterization and molecular cloning of human hepatic lysosomal acid lipase," Eur. J. Biochem., vol. 219(3) (1994) pp. 905-914.
Anderson et al., "Lysosomal acid lipase mutations that determine phenotype in Wolman and cholesterol ester storage disease," Mol. Genet. Metab., vol. 68(3) (1999) pp. 333-345.
Anderson, et al., "In Situ Localization of the Genetic Locus Encoding the Lysosomal Acid Lipase/Cholesteryl Esterase (LIPA) Deficient in Wolman Disease to Chromosome 10q23.2-q23.3," Genomics 15:245-247 (1993).
Anderson, et al., "Mutations at the lysosomal acid cholesteryl ester hydrolase gene locus in Wolman disease," PNAS 91:2718-2722 (1994).
Anderson, N. et al., "Molecular Mechanisms and Therapeutic Targets in Steatosis and Steatohepatitis," Pharmacological Reviews, 2008, vol. 60, pp. 311-357.
Anderson, R.A. et al., "Cloning and expression of cDNA encoding human lysosomal acid lipase/cholesteryl ester hydrolase, similarities to gastric and lingual lipases," The Journal of Biological Chemistry, vol. 266(33) (Nov. 25, 1991) pp. 22479-22484.
Arterburn, et al., "Orthotopic Liver Transplantation for Cholesteryl Ester Storage Disease," J. Clin. Gastroenterlogy, 13:482-485 (1994).
Aslanidis, et al., "Genetic and Biochemical Evidence that CESD and Wolman Disease Are Distinguished by Residual Lysosomal Acid Lipase Activity," Genomics 33:85-93 (1996).
Aslanidis, et al., "Genomic Organization of the Human Lysosomal Acid Lipase Gene (LIPA)," Genomics, 20:329-331 (1994).
Assman, G. et al., The Metabolic and Molecular Bases of Inherited Disease, $7^{th}$ Ed. (1995) pp. 2563-2587.
Assmann, G. et al., "Chapter 142: Acid Lipase Deficiency: Wolman Disease and Cholesteryl Ester Storage Disease," Part 16: Lysosomal Disorders, The McGraw-Hill Companies, Inc., 2001, pp. 1-49.
Asumendi, et al., "Hepatic Sinusoidal Endothelium Heterogeneity with Respect to Mannose Receptor Activity is Interleukin-1 Dependent," 23(6):1521-1529 (1996).
Attiga et al., "Inhibitors of Prostaglandin Synthesis Inhibit Human Prostate Tumor Cell Invasiveness and Reduce the Release of Matrix Metalloproteinases," Cancer Research, Aug. 15, 2000, vol. 60, pp. 4629-4637.
Avart, et al., "Cholesteryl Ester Hydrolysis in J774 Macrophages Occurs in the Cytoplasm and Lysosomes," Journal of Lipid Research, 40:405-414 (1999).
Baenziger, et al., "Structural Determinants of Concanavalin a Specificity for Oligosaccharides," 254(7):2400-2407 (1979).
Bailey, "An overview of Enzyme Replacement Therapy for Lysosomal Storage Diseases," The Online Journal of Issues in Nursing, 2008, vol. 13, No. 1, Manuscript 3, pp. 1-14.
Barton, et al., "Replacement Therapy for Inherited Enzyme Deficiency—Macrophage Targeted Glucocerebrosidase for Gaucher's Disease," The New England journal of Medicine, pp. 1464-1470 (1991).
Barton, et al., "Therapeutic Response to Intravenous Infusions of Glucocerebrosidase in a Patient with Gaucher Disease," 87:1913-1916 (1990).
Beaudet et al., "Acid lipase in cultured fibroblasts: cholesterol ester storage disease," J. Lab. Clin. Med., 84:54-55 (1974).
Beaudet, et al., "Cholesterol Ester Storage Disease: Clinical, Biochemical, and Pathological Studies," The Journal of Pediatrics, 90(6):910-914 (1977).
Begley, et al., "Lysosomal Storage Diseases and the Blood-Brain Barrier," Current Pharmaceutical Design, 14:1566-1580 (2008).

Bennett, M.K et al., "Sterol Regulation of Fatty Acid Synthase Promoter Coordinate Feedback Regulation of Two Major Lipid Pathways," The Journal of Biological Chemistry, vol. 270 (1995) pp. 25578-25583.
Bertrand, et al., "Transport Characteristics of a Novel Peptide Platform for CNS Therapeutics," J Cell. Molecular Medicine, 14(12):2827-2839 (2010).
Besley, et al., "Cholesterol ester storage disease in an adult presenting with sea-blue histiocytosis" Clinical Genetics, 1984, vol. 26, pp. 195-203.
Beutler, et al., "Enzyme Replacement Therapy for Gaucher Disease," Blood, 78(5):1183-1189 (1991).
Bhakdi et al., "On the Pathogenesis of Atherosclerosis: Enzymic Transformation of Human Low-Density Lipoprotein to an Atherogenic Moiety," Journal of Experimental Medicine, vol. 182(6) (1995) pp. 1959-1971.
Biggs, H.G. et al., "A Manual Colorimetric Assay of Triglycerides in Serum" Clinical Chemistry, vol. 21, No. 3,(1975), pp. 437-441.
Bijsterbosch, M.K. et al., "Quantitative Analysis of the Targeting of Mannose-Terminal Glucocerebrosidase, Predominant Uptake by Liver Endothelial Cells" European Journal of Biochemistry, Apr. 1996, vol. 237(2), pp. 344-349.
Bindu, et al., "Cholesterol Ester Storage Disease with Unusual Neurological Manifestations in Two Siblings: A Report from South India," journal of Child Neurology, 22(12):1401-1404 (2007).
Boldrini, et al., "Wolman disease and cholesteryl ester storage disease diagnosed by histological and ultrastructural examination of intestinal and liver biopsy," Path. Res. Practice 200:231-240 (2004).
Bond, et al., "Antiatherogenic Properties of Calcium Antagonists," J. Cardiovasc. Pharmacol., vol. 17 (Suppl. 4)(1991) pp. S87-S93.
Brady, et al., "modifying Exogenous Glucocerebrosidase for Effective Replacement Therapy in Gaucher Disease," J. Inher. Metab. Dis., 17:510-519 (1994).
Brea, A. et al., "Nonalcoholic fatty liver disease is associated with carotid atherosclerosis—A case-control study," Arteriosclerosis Thrombosis and Vascular Biology, May 2005, vol. 25(5), pp. 1045-1050.
Brecher, et al., "Effect of Atherosclerosis on Lysosomal Cholesterol Esterase Activity in Rabbit Aorta," Journal of Lipid Research, 18:154-160 (1977).
Briggs, et al., "Nuclear Protein that Binds Sterol Regulatory Element of Low Density Lipoprotein Receptor Promoter," 268(19):14490-14496 (1993).
Brown et al., "Use of Nile Red Stain in the Detection of Cholesteryl Ester Accumulation in Acid Lipase-Deficient Fibroblasts," Arch Pathol Lab Med, 112:295-296 (1988).
Brown, et al., "A Receptor-Mediated Pathway for Cholesterol Homeostasis," Science, 232(4746):34-47 (1986).
Brown, et al., "Multivalent Feedback Regulation of HMG CoA Reductase, a Control Mechanism Coordinating Isoprenoid Synthesis and Cell Growth," journal of Lipid Research, 21:505-517 (1980).
Brown, M.S. et al., "Restoration of a Regulatory Response to Low Density Lipoprotein in Acid Lipase-deficient Human Fibroblast," The Journal of Biological Chemistry, vol. 251(11) (Jun. 10, 1976) pp. 3277-3286.
Brown, M.S. et al., "The SREBP Pathway: Regulation of Cholesterol Metabolism by Proteolysis of a Membrane-Bound Transcription Factor," Cell, vol. 89 (1997) pp. 331-340.
Brumshtein, et al., "Characterization of Gene-Activated human Acid-β-Glucosidase: Crystal Structure, Glycan Composition, and Internalization into Macrophages," Glycobiology, 20(1):24-32 (2010).
Brumshtein, et al., "Structural Comparison of Differently Glycosylated Forms of acid-β-Glucosidase, the defective Enzyme in Gaucher Disease," Acta Crystallographica Section D, 62:1458-1465 (2006).
Burke, et al., "Deficient Activity of Hepatic Acid Lipase in Cholesterol Ester Storage Disease," Science 176(4032):309-310 (1972).
Burton, et al., "Acid Lipase Cross-Reacting Material in Wolman Disease and Cholesterol Ester Storage Disease," Am j Hum Genet, 33:203-208 (1981).
Burton, et al., "Lysosomal Acid Lipase in Cultivated Fibroblasts: Characterization of Enzyme Activity in Normal and Enzymatically Deficient Cell Lines," Clinica Chimica Acta, 101:25-32 (1980).
Burton, et al., "Purification and Properties of Human Placental Acid Lipase," Biochimica et Biophysica Acta, 618:449-460 (1980) (Abstract).

(56) References Cited

OTHER PUBLICATIONS

Byrd, et al., "Wolman's Disease: Ultrastructural Evidence of Lipid Accumulation in Central and Peripheral Nervous Systems," Acta Neuropathol, 45:37-42 (1979).
Cagle, P.T., et al, "Clinicapathologic Conference: Pulmonary Hypertension in an 18-Year-Old Girl with Cholesteryl Ester Storage Disease (CESD)" American Journal of Medical Genetics, 1986 vol. 24, pp.711-722.
Carter et al., "Cholesterol Ester Storage Disease," Pediat. Radiol, 2:135-136 (1974).
Carter, et al., "Design and synthesis of sulfonyl-substituted 4,5-diarylthiazoles as selective cyclooxygenase-2 inhibitors," Bioorganic & Medicinal Chemistry Letters, 1999, vol. 9(8), pp. 1167-1170.
Carter, J. et al., "Synthesis and activity of sulfonamide-substituted 4,5-diaryl thiazoles as selective cyclooxygenase-2 inhibitors," Bioorganic & Medicinal Chemistry Letters, 1999, vol. 9(8), pp. 1171-1174.
Chan, et al., "Prostaglandins, Prostacyclin, and Thromboxane in Cardiovascular Diseases," Drug Development Research, vol. 7(4) (1986) pp. 341-359.
Chatrath, et al., "Cholesterol Ester Storage Disease (CESD) Diagnosed in an Asymptomatic Adult," Dig. Dis. Sci. 54:168-173 (2009).
Chatterjee, S. et al., "Evaluation of urinary cells in acid cholesteryl ester hydrolase deficiency," Clinical Genetics, vol. 29 (1986) pp. 360-368.
Chauret et al., "In Vitro metabolism considerations, including activity testing of metabolites, in the discovery and selection of the COX-2 inhibitor etoricoxib," Bioorganic & Medicinal Chemistry Letters, 2001, vol. 11(8), pp. 1059-1062.
Chin, J. et al., "Evidence for Coordinate Expression of 3-Hydroxy-3-methylglutaryl Coenzyme a Reductase and Low-Density Lipoprotein Binding Activity," The Journal of Biological Chemistry, vol. 256, No. 12, 1981, pp. 6304-6310.
Chobanian, et al., "Effects of Hypertension and of Antihypertensive Therapy on Atherosclerosis," Suppl. I. Hypertension, 8(4):15-21 (1986).
Chowdhury, et al., "A Fourteen Years Old Boy with Cholesterol Ester Storage Disease," J Medicine, 10:146-148 (2009).
Christomanou, et al., "Prenatal Monitoring for Wolman's Disease in a Pregnancy at Risk," Clinical Case Reports, 57 :440-441 (1981).
Coates, et al., "Prenatal diagnosis of Wolman disease," American Journal of Medical Genetics, 2:397-407 (1978).
Coates, P.M. et al., "Genetic Variation of Human Mononuclear Leukocyte Lysosomal Acid Lipase Activity—Relationship to Atherosclerosis," Atherosclerosis, vol. 62, 1986, pp. 11-20.
Coelho et al., "Cholesterylester Storage Disease Report of a case," Arq Gastroenterol, 24(3/4):184-187, (1987).
Colin, et al., "Modification of Pancreatic Lipase Properties by Directed Molecular Evolution," Protein Engineering, Design and Selection, pp. 1-9, (2010) downloaded from peds.oxfordjournals.org.
Collantes, R. et al., "Nonalcoholic fatty liver disease and the epidemic of obesity," Cleveland Clinic Journal of Medicine, Aug. 2004, vol. 71, No. 8, pp. 657-664.
Cortner, et al., "Genetic Variation of Lysosomal Acid Lipase," Pediatric Research, 10:927-932 (1976).
Cox, "Effect of Lysosomal Cholesterol Accumulation on Lysosomal and Vacuolar-Atpase Activity," Submitted to the Faculty of the Graduate School of Vanderbilt university, p. 1-108 (2007).
Crocker, et al., "Wolman's Disease: Three New Patients with a Recently Described Lipidosis," Pediatrics, 35:627-640 (1965).
Cummings, et al., "Increased Hepatic Secretion of Very-Low-Density Lipoprotein Apolipoprotein B-100 in Choesteryl Ester Storage Disease, 41(1):111-114 (1995).
D'Agostino, et al., "Cholesterol Ester Storage Disease: Clinical, Biochemical, and pathological Studies of Four New Cases," Journal of Pediatric Gastroenterology and Nutrition, 7:446-450 (1988).
Dahl, et al., "Hepatosplenomegalic Lipidosis: What Unless Gaucher? Adult Cholesteryl Ester Storage Disease (CESD) with Anemia, Mesenteric Lipodystrophy, Increased Plasma Chitotriosidase Activity and a homozygous lysosomal Acid Lipase—1 Exon 8 / Splice Junction Mutation," Journal of Hepatology 31:741-746 (1999).
Dalgic, "Cholestryl ester storage disease in a young child presenting as isolated hepatomegaly treated with simvastatin," The Turkish journal of Pediatrics, 2006, vol. 48, pp. 148-151.
Daly, et al., "Neonatal Gene Transfer Leads to Widespread Correction of Pathology in a Murine Model of Lysosomal Storage Disease," Proc. Natl. Acad., 96:2296-2300 (1999).
Davis, et al., "role of Acid Lipase in Cholesteryl Ester Accumulation During Atherogenesis; Correlation of Enzyme Activity with Acid Lipase-Containing Macrophages in Rabbit and Human Lesions," Atherosclerosis, 55:205-215 (1985).
De Duve, "The Participation of Lysosomes in the Transformation of Smooth Muscle Cells to Foamy Cells in the Aorta of Cholesterol-Fed Rabbits," Acta Cardiologica Suppl., pp. 9-25 (1975).
De Grey, et al., "Medical Bioremediation: Prospects for the Application of Microbial Catabolic Diversity to aging and Several Major Age-Related Diseases," Ageing Research Reviews, 4:315-338 (2005).
Decarlis, et al., "Combined Hyperlipidaemia as a Presenting Sign of Cholesteryl Ester Storage Disease," JIMD Short Report, Online, 3 pages (2009).
Desai, et al., "Cholesteryl Ester Storage Disease: Pathologic Changes in an Affected Fetus," American Journal of Medical Genetics, vol. 26, pp. 689-698 (1987).
Desnick, et al., "Advances in the Treatment of Inherited Metabolic Disease," Chapter 5, pp. 281-369 (1981).
Desnick, R.J. et al., "Enzyme replacement and enhancement therapies: lessons from lysosomal disorder," Nat. Rev. Genet., vol. 3 (2002) pp. 954-966.
Desnick, R.J. et al., "Toward Enzyme Therapy for Lysosomal Storage Diseases," Physiological Reviews, Jan. 1976, vol. 56, No. 1, pp. 57-93.
Di Bisceglie, "Cholesteryl Ester Storage Disease: Hepatopathology and Effects of Therapy with Lovastatin," Hepatology, 11 (5), pp. 764-772 (1990).
Dietschy, J.M., "LDL Cholesterol: Its Regulation and Manipulation," Hospital Practice (Jun. 1990) pp. 67-78.
Dincsoy et al., "Cholesterol Ester Storage Disease and Mesenteric Lipodystrophy," Am. J. Pathol., 81:263-264 (1984).
Dobson, "Gene therapy progress and prospects: magnetic nanoparticle-based gene delivery," Gene Ther., vol. 13(4) (2006) pp. 283-287.
Doebber, et al., "Enhanced Macrophage Uptake of Synthetically Glycosylated Human Placental β-Glucocerebrosidase," The Journal of Biological Chemistry, vol. 257(5), pp. 2193-2199 (1982).
Drebber, et al., "Severe Chronic Diarrhea and Weight Loss in Cholesteryl Ester Storage Disease: A Case Report," World Journal Gastroenterol, 2005, vol. 11 (15), pp. 2364-2366.
Drevon et al., "The Effects of Cholesterol/Fat Feeding on Lipid Levels and Morphological Structures in Liver, Kidney and Spleen in Guinea Pigs," Acta Path. Microbial. Scand. Sect. A, 85:1-18 (1977).
Du, H., "Reduction of Atherosclerotic Plaques by Lysosomal Acid Lipase Supplementation," Arterioscler Thromb Vasc Biol., vol. 24, pp. 147-154 (2004).
Du, H., et al., "Lysosomal Acid Lipase-Deficient Mice: Depletion of White and Brown Fat, Severe Hepatosplenomegaly, and Shortened Life Span," Journal of Lipid Research, vol. 42(4), pp. 489-500 (2001).
Du, H., et al., "Enzyme therapy for lysosomal acid lipase deficiency in the mouse" Human Molecular Genetics, 2001, vol. 10, No. 16, pp. 1639-1648.
Du, H., et al., "Enzyme therapy for lysosomal acid lipase deficiency in the mouse model" The American Journal of Human Genetics, Oct. 2000, vol. 67, No. 4, Supp. 2, pp. 427, Abstract 2409.
Du, H., et al., "Human Transcription Factor USF Stimulates Transcription through the Initiator Elements of the HIV-1 and the Ad-ML Promoters," The EMBO Journal, vol. 12(2), pp. 501-511 (1993).
Du, H., et al., "Lysosomal Acid Lipase and Atherosclerosis," Curr. Opin. Lipidol., vol. 15, pp. 539-544 (2004).
Du, H., et al., "Lysosomal acid lipase deficiency: correction of lipid storage by adenovirus-mediated gene transfer in mice," Hum. Gene Ther., vol. 13(11) (2002) pp. 1361-1372.

(56) References Cited

OTHER PUBLICATIONS

Du, H., et al., "Molecular and enzymatic analyses of lysosomal acid lipase in cholesteryl ester storage disease," Mol. Genet. Metab., vol. 64(2) (1998) pp. 126-134.

Du, H., et al., "Mouse lysosomal acid lipase: characterization of the gene and analysis of promoter activity," Gene, vol. 208, 1998, pp. 285-295.

Du, H., et al., "MRI of Fat Distribution in a Mouse Model of Lysosomal Acid Lipase Deficiency," AJR 184:658-662 (2005).

Du, H., et al., "Targeted disruption of the mouse lysosomal acid lipase gene: long-term survival with massive cholesteryl ester and triglyceride storage," Human Molecular Genetics, vol. 7 (1998) pp. 1347-1354.

Du, H., et al., "The role of mannosylated enzyme and the mannose receptor in enzyme replacement therapy" The American Journal of Human Genetics, Dec. 2005, vol. 77, pp. 1061-1074.

Du, H., et al., "Tissue and cellular specific expression of murine lysosomal acid lipase mRNA and protein," Journal of Lipid Research, vol. 37(9) (1961) pp. 937-949.

Du, H., et al., Two Polymorphic Forms of Human Lysosomal Acid Lipase Have Different Level of Activity, Amer. J. Human Genet, vol. 57 (1995) (Abstract).

Du, H., et al., "Wolman disease/cholesteryl ester storage disease: efficacy of plant produced human lysosomal acid lipase in mice," Journal of Lipid Research, vol. 49, 2008, pp. 1646-1657.

Dustin, et al., "A Mannose 6-Phosphate-Containing N-Linked Glycopeptide Derived from Lysosomal Acid Lipase is Bound to MHC Class II in B Lymphoblastoid Cell Lines," J. Immunol., vol. 156, pp. 1841-1847 (1996).

Edelstein, et al., "Cholesteryl Ester Storage Disease: A Patient with Massive Splenomegaly and Splenic Abscess," The American Journal of Gastroenterology, 83:687-688. (1988).

Elleder et al., "Lysosomal Acid Lipase Deficiency. Overview of Czech Patients," Cas Lek Cesk, 13(23),719-724 (1999).

Elleder et al., "Subclinical course of cholesterol ester storage disease (CESD) diagnosed in adulthood," Virchows Archie a Pathological Anatomy and Histopathology, 416:3457-365 (1990).

Elleder, et al., "Subclinical Course of Cholesteryl Ester Storage Disease in an Adult with Hypercholesterolemia, Accelerated Atherosclerosis, and Liver Cancer," Journal of Hepatology, vol. 32, pp. 528-534 (2000).

Elleder, et al., "Testis—A Novel Storage Site in Human Cholesteryl Ester Storage Disease Autopsy Report of an Adult Case with a Long-Standing Subclinical Course Complicated by Accelerated Atherosclerosis and Liver Carcinoma," Virchows Arch, vol. 436, pp. 82-87 (2000).

Endres, M. et al., "Stroke protection by 3-hydroxy-3-methylglutaryl (HMG)-CoA reductase inhibitors mediated by endothelial nitric oxide synthase," Proc. Natl. Acad. Sci., Jul. 1998, vol. 95, pp. 8880-8885.

Ericsson, J. et al., "Identification of Glycerol-3-phosphate Acyltransferase as an Adipocyte Determination and Differentiation Factor 1- and Sterol Regulatory Element-binding Protein-responsive Gene," The Journal of Biological Chemistry, vol. 272, No. 11, 1997, pp. 7298-7305.

Ericsson, J. et al., "Sterol regulatory element binding protein binds to a cis element in the promoter of the farnesyl diphosphate synthase gene," Proc. Natl. Acad. Sci. USA, vol. 93 (1996) pp. 945-950.

Escary, et al., "Hormone-Sensitive Lipase Overexpression Increases Cholesteryl Ester Hydrolysis in Macrophage Foam Cells," Arteriosclerosis, Thrombosis, and Vascular Biology, vol. 18(6) (1998) pp. 991-998.

Escary, J.L. et al., "Paradoxical effect on atherosclerosis of hormone-sensitive lipase overexpression in macrophages," Journal of Lipid Research, vol. 40 (1999) pp. 397-404.

Essa, et al., "Wolman Disease: A Review," Curr. Paed. Res., vol. 3(1), pp. 1-12 (1999).

Ezekowitz, et al., "Molecular Characterization of the Human Macrophage Mannose Receptor: Demonstration of Multiple Carbohydrate Recognition-Like Domains and Phagocytosis of Yeasts in Cos-1 Cells," J. Exp. Med., vol. 172, pp. 1785-1794 (1990).

Ezekowitz, et al., "The Structure and Function of Vertebrate Mannose Lectin-Like Proteins," J. Cell. Sci. Suppl., vol. 9, pp. 121-133 (1988).

Fadden, et al., "Molecular Characterization of the Rat Kupffer Cell Glycoprotein Receptor," Glycobiology, vol. 13(7), pp. 529-537 (2003).

Ferry et al., "Liver Transplantation for Cholesteryl Ester Storage Disease," Journal of Pediatric Gastroenterology and Nutrition, 12:376-378 (1991).

Fielding, C.J. et al., "Intracellular cholesterol transport," J. Lipid. Res., vol. 38 (1997) pp. 1503-1521.

Fiete, et al., "The macrophage/endothelial cell mannose receptor cDNA encodes a protein that binds oligosaccharides terminating with S04-4-GalNAc,31,4BlcNAcf3 or Man at independent sites," Proc. Natl. Acad. Sci., vol. 94, pp. 11256-11261 (1997).

Fitoussi, et al., "New Pathogenetic Hypothesis for Wolman Disease: Possible Role of Oxidized Low-Density Lipoproteins in Adrenal Necrosis and Calcification," Biochem, J., vol. 301, pp. 267-273 (1994).

Fitzky et al., "7-Dehydrocholesterol-Dependent Proteolysis of HMG-CoA Reductase Suppresses Sterol Biosynthesis in a Mouse Model of Smith-Lemli-Opitz/RSH Syndrome," The Journal of Clinical Investigation, 108(6):905-915 (2001).

Fleckenstein, A., "History of Calcium Antagonists," Circulation Research, Feb. 1983, vol. 52(2), pp. I-3-I-16.

Fluiter, K. et al., "In Vivo Regulation of Scavenger Receptor BI and the Selective Uptake of High Density Lipoprotein Cholesteryl Esters in Rat Liver Parenchymal and Kupffer Cells," J. Bio. Chem., vol. 273 (14) (Apr. 3, 1998) pp. 8434-8438.

Foger et al., "Unusual Presentation of Cholesterol Ester Storage Disease (CESD): Report on New Family," Atherosclerosis, 109:132 Abstract 155 (1994).

Folch, J. et al., "A Simple Method for the Isolation and Purification of Total Lipids from Animal Tissues," McLean Hospital Research Laboratories (1956) pp. 497-509.

Friedman et al., "A Comparison of the Pharmacological Properties of Carbohydrate Remodeled Recombinant and Placental-Derived b-Glucocerebrosidase: Implications for Clinical Efficacy in Treatment of Gaucher Disease," Blood, 93(9):2807-2816 (1999).

Fujimoto, T., "Lipid droplets: a classic organelle with new outfits," Histochem Cell Biol, 2008, vol. 130, pp. 263-279.

Fujiyama et al., "A New Mutation (LIPA Tyr22X) of Lysosomal Acid Lipase Gene in a Japanese Patient with Wolman Disease," Human Mutation, 8:377-380 (1996).

Fulcher, et al., "Pediatric Case of the Day", RadioGraphics, 18(2):533-534 (1998).

Furbish et al., "Uptake and Distribution of Placental Glucocerebrosidase in Rat Hepatic Cells and Effects of Sequential Deglycosylation," Biochimica et Biophysica Acta, 673 425-434, 1981.

Gasche et al., "A Novel Variant of Lysosomal Acid Lipase in Cholesteryl Ester Storage Disease Associated with Mild Phenotype and Improvement on Lovastatin," Journal of Hepatology, 27:744-750 (1997).

GenBank: CAA54026.1 Protein Translations of Life, Host: NCVI PubMed Mar. 29, 1993.

Gene ID: 3988, LIPA lipase A, lysosomal acid, cholesterol esterase [*Homo sapiens*], Jun. 23, 2012 [Summary].

Gerlai et al., "Gene-Targeting Studies of Mammalian Behavior: Is it the Mutation or the Background Genotype," Trends Neurosci, 19:177-181 (1996).

Gidiri et al., "Congenital cholesteryl ester storage disease: What are the implications in pregnancy?" Letter to the Editor, European Journal of Obstetrics and Gynecology and Reproductive Biology, 142:81-87 (2009).

Ginsberg et al., Suppression of Apolipoprotein B Production during Treatment of Cholesteryl Ester Storage Disease with Lovastatin, J. Clin. Invest., 80:1692-1697 (1987).

Ginsberg, H. et al., "Reduced plasma concentrations of total, low density lipoprotein and high-density lipoprotein cholesterol in patients with Gaucher type I disease," Clinical Genetics, 1984, vol. 26, pp. 109-116.

(56) References Cited

OTHER PUBLICATIONS

Glueck et al., "Safety and Efficacy of Treatment of Pediatric Cholesteryl Ester Storage Disease with Lovastatin," Pediatric Research, 32:559-565 (1992).
Goldstein, J.L. et al., "Receptor-Mediated Endocytosis of Low-Density Lipoprotein in Cultured Cells," Methods in Enzymology, vol. 98 (1983) pp. 241-260.
Goldstein, J.L. et al., "Regulation of the mevalonate pathway," Nature, vol. 343 (Feb. 1, 1990) pp. 425-430.
Goldstein, J.L. et al., "Role of Lysosomal Acid Lipase in the Metabolism of Plasma Low Density Lipoprotein," J. Biol. Chem., vol. 250 (21) (1975) pp. 8487-8495.
Goodman, J.M.,"Demonstrated and inferred metabolism associated with cytosolic lipid droplets," Journal of Lipid Research, 2009, vol. 50, pp. 2148-2156.
Grabowski et al., "Enzyme Therapy for Lysosomal Storage Disease: Principles, Practice and Prospects," Annu. Rev. Genomics Hum. Genet., 4:403-436 (2003).
Grabowski, G.A., et al, "Enzyme supplementation for treatment of arthero-/arterio-sclerosis using lysosomal acid lipase (LAL)" The American Journal of Human Genetics, Oct. 2000, vol. 67, No. 4, Supp. 2, pp. 38 (Abstract No. 136).
Grabowski, G.A., et al., "Acid β-Glucosidase: Enzymology and Molecular Biology of Gaucher Disease," Biochemistry and Molecular Biology, 1990, vol. 25, Issue 6, pp. 385-414.
Grabowski, GA., et al, "Enzyme Therapy in Type I Gaucher Disease: Comparative Efficacy of Mannose-terminated Glucocerebrosidase from Natural and Recombinant Sources," Annals of Internal Medicine, 1995, vol. 122, pp. 33-39.
Grabowski, Gregory, "Enzyme replacement therapy corrects Lysosomal Acid Lipase Deficiency (LALD) in a mouse model of Wolman disease/cholesteryl ester storage disease," Abstracts / Molecular Genetics and Metabolism, vol. 102, 2011, pp. S19.
Groener, J.E.M. et al., "Metabolic fate of oleic acid derived from lysosomal degradation of cholesteryl oleate in human fibroblasts," Journal of Lipid Research, 1996, vol. 37, pp. 2271-2279.
Groener, J.E.M., et al., "Difference in substrate specificity between human and mouse lysosomal acid lipase: low affinity for cholesteryl ester in mouse lysosomal acid lipase," Biochimica et Biophysica Acta, 2000, vol. 1487, pp. 155-162.
Guazzi et al., "Wolman's Disease. Distribution and Significance of the Central Nervous System lesions," Path. Europ., 3:266-277 (1968).
Gunning et al., "Isolation and Characterization of Full-Length cDNA Clones for Human a-, 13-, and y-Actin mRNAs: Skeletal but Not Cytoplasmic Actins Have an Amino-Terminal Cysteine that is Subsequently Removed," Molecular and Cellular Biology, 3(5):787-795 (1983).
Guzzetta et al., "Elective Subtotal Splenectomy," Ann. Surg., 211 (1): 34-42 (1990).
Haemmerle, G. et al., "Letting lipids go: hormone-sensitive lipase," Current Opinion in Lipidology, vol. 14 (2003) pp. 289-297.
Hafner et al., "The Human Primary Hepatocyte Transcriptome Reveals Novel Insights into Atorvastatin and Rosuvastatin Action," Pharmacogenetics and Genomics, 21(11):741-750 (2011).
Hakala, J.K. et al. "Lysosomal Enzymes are Released from Cultured Human Macrophages, Hydrolyze LDL in Vitro, and Are Present Extracellularly in Human Atherosclerotic Lesions," Arteriosclerosis, Thrombosis, and Vascular Biology, 2003, vol. 23, pp. 1430-1436.
Haller et al., "Gallbladder Dysfunction in Cholesterol Ester Storage Disease," JPGN, 50(5):556-557 (2010).
Hatanaka et al., "Human IgA-Binding Peptides Selected from Random Peptide Libraries: Affinity Maturation and Application in IgA Purification," J. Bio. Chem. in Press, M112 389742, pp. 1-12 (2012).
Heinz et al., "Identification and in Situ Localization of the Insulin-Like Growth FactorII/Mannose-6-Phosphate (IGF-II/M6P) Receptor in the Rat Gastrointestinal Tract: Comparison with the IGF-1 Receptor," U.S. National Institutes of Health, 129(4):1769-1778 (1991).
Hill et al., "CT Findings in Acid Lipase Deficiency: Wolman Disease and Cholesteryl Ester Storage Disease," Journal of Computer Assisted Tomography, 7(5):815-818 (1983).
Hirschowitz, E.A., et al., "Regional treatment of hepatic micrometastasis by adenovirus vector-mediated delivery of interleukin-1 and interleukin-12 cDNAs to the hepatic parenchyma," Cancer Gene Therapy, 1999, vol. 6, No. 6, pp. 491-498.
Hoeg et al., "Characterization of Neutral and Acid Ester Hydrolase in Wolman's Disease," Biochimica et Biophysica Acta, 711:59-65 (1982).
Hoeg et al., "Cholesteryl Ester Storage Disease and Wolman Disease: Phenotypic Variants of Lysosomal Acid Cholesteryl Ester Hydrolase Deficiency," Am. J. Hum. Genet, 36:1190-1203 (1984).
Holbrook et al., "Tolerization as a Tool for Generating Novel Monoclonal Antibodies," Immunology and Cell Biology, 80:319-322 (2002).
Hollak, C.E. et al., "Alglucerase: Practical Guidance on Appropriate Dosage and Administration in Patients with Gaucher Disease," Bio Drugs, vol. 9(1) (1998) pp. 11-23.
Hooper et al., "A Novel Missense LIPA Gene Mutation, N98S, in a Patient with Cholestelyl Ester Storage Disease," Clinica Chimica Acta, 398:152-154 (2008).
Hopkins et al., "Human Genetics and Coronary Heart Perspective," Annu. Rev. Nutr., 9:303-45 (1989).
Hsu et al., "The Cyclooxygenase-2 Inhibitor Celecoxib Induces Apoptosis by Blocking Akt Activation in Human Prostate Cancer Cells Independently of Bcl-2," The Journal of Biological Chemistry, Apr. 14, 2000, vol. 275, No. 15, pp. 11397-11403.
Hua, X. et al., "SREBP-2, a second basic-helix-loop-helix-leucine zipper protein that stimulates transcription by binding to a sterol regulatory element," Proc. Natl. Acad. Sci., vol. 90 (1993) pp. 11603-11607.
Hua, X. et al., "Structure of the Human Gene Encoding Sterol Regulatory Element Binding Protein-1 (SREBF1) and Localization of SREBF1 and SREBF2 to Chromosomes 17p11.2 and 22q13," Genomics, vol. 25 (1995) pp. 667-673.
Ikeda, et al., "Production of Recombinant Human Lysosomal Acid Lipase in Schizosaccharomyces pombe: Development of a Fed-Batch Fermentation and Purification Process," J. of Bioscience and Bioengineering, 98:366-373 (2004).
Imanaka et al., "Characterization of Lysosomal Acid Lipase Purified from Rabbit Liver," J. Biochem. 96:1089-1101 (1984).
Ishibashi, S. et al "Hypercholesterolemia in Low Density Lipoprotein Receptor Knockout Mice and its Reversal by Adenovirus-mediated Gene Delivery," J. Clin. Invest., Aug. 1993, vol. 92, pp. 883-893.
Ishibashi, S. et al., "Massive Xanthomatosis and Atherosclerosis in Cholesterol-fed Low-Density Lipoprotein Receptor-negative Mice," J. Clin. Invest., May 1994, vol. 93, pp. 1885-1893.
Iverson et al., "Asymptomatic cholesteryl ester storage disease in an adult controlled with simvastatin," Ann Clin Biochem, 34:433-436 (1997).
Jackson, L. et al., "COX-2 Selective Nonsteroidal Anti-lnflammatory Drugs: Do They Really Offer Any Advantages?", Drugs, Jun. 2000, vol. 59(6), pp. 1207-1216.
Jeschke et al., "Cholesteryl Ester Storage Disease, Clinical and Morphological Aspects," Cholesterylester-Speicherkrankheit, 120(8):601-604 (1982).
Jeyakumar, et al., "Storage Solutions: Treating Lysosomal Disorders of the Brain," Nature Reviews Neuroscience,6:713-725 (2005).
Jian, B. et al., "Scavenger Receptor Class B Type I as a Mediator of Cellular Cholesterol Efflux to Lipoproteins and Phospholipid Acceptors," J. Bio. Chem., vol. 273(10), (1998) pp. 5599-5606.
Jirtle et al., "Modulation of Insulin-Like Growth Factor-II/Mannose 6-Phosphate Receptors and Transforming Growth Factor-131 during Liver Regeneration," The Journal of Biological Chemistry, 266(33):22444-22450 (1991).
Johnson, M.S.C. et al., "Characterization and Chromosomal Localization of Rat Scavenger Receptor Class B Type 1, a High-Density

(56) References Cited

OTHER PUBLICATIONS

Lipoprotein Receptor with a Putative Leucine Zipper Domain and Peroxisomal Targeting Sequence," Endocrinology, vol. 139(1) (1998) pp. 72-80.
Johnson-Saliba et al., "Gene therapy: optimizing DNA delivery to the nucleus," Curr. Drug Targets, vol. 2(4) (2001) pp. 371-399.
Jolly et al., "Lysosomal Storage Diseases of Animals: An Essay in Comparative Pathology," Vet Pathol., 34:527-548 (1997).
Justus et al., "Lebermorphologie und Klinik eins Falls von Cholesterinester-Speicherkrankheit," Dtsch. Z. Verdau-Stoffwechs. krankh. 48:198-207 (1988).
Kahana et al., "Primary Familial Xanthomatosis with Adrenal Involvement (Wolman's Disease); Report of a further Case with Nervous System Involvement and pathogenetic Considerations," Pediatrics, 42(1):71-76 (1968).
Kale et al., "End Stage Renal Disease in a Patient with Cholesteryl Ester Storage Disease Following Successful Liver Transplantation and Cyclosporine immunosuppression," Journal of Pediatric Gastroenterology and Nutrition, 20:95-97 (1995).
Kawashiri, M. et al., "Gene therapy for lipid disorders," Curr Control Trials Cardiovasc Med, 2000, vol. 1, pp. 120-127.
Kelly et al., "Characterization of Plasma Lipids and Lipoproteins in Cholesteryl Ester Storage Disease," Biochemical Medicine, 33:29-37 (1985).
Kikuchi et al., "Evaluation of Jejunal Function in Wolman's Disease," Journal of Pediatric Gastroenterology and Nutrition, 12(1): 6569 (1991).
Kim, "Successful Management of Difficult Infusion-Associated Reactions in a Young Patient with Mucopolysaccharidosis Type VI Receiving Recombinant Human Arylsulfatase B (Galsulfase [Naglazyme])," Pediatrics, 2008, vol. 121, No. 3, pp. 714-717.
Kim, J.B. et al., "ADD1/SREBP1 promotes adipocyte differentiation and gene expression linked to fatty acid metabolism," Genes. Dev., vol. 10 (1996) pp. 1096-1107.
Kirk, E.A et al., "Hyper- and hypo-responsiveness to dietary fat and cholesterol among inbred mice: searching for level and variability genes," Journal of Lipid Research, 1995, vol. 36, pp. 1522-1532.
Klima et al., "A Splice Junction Mutation Causes Deletion of a 72-Base Exon from the mRNA for Lysosomal Acid Lipase in a Patient with Cholesteryl Ester Storage Disease," J. Clin. Invest., 92:2713-2718 (1993).
Koch et al., "Assignment of LIPA, Associated with Human Acid Lipase Deficiency, to Human Chromosome 10 and Comparative Assignment to Mouse Chromosome 19," Somatic Cell Genetics, 7(3):345-358 (1981).
Kodlitsch et al., "Splice-Site Mutations in Atherosclerosis Candidate Genes Relating Individual Information to Phenotype," Circulation, 100:693-699 (1999).
Koffel et al., "The *Saccharomyces cerevisiae* YLL012/YEH1, YLR020/YEH2, and TGL1 genes encode a novel family of membrane-anchored lipases that are required for steryl ester hydrolysis," Mol. Cell Biol., vol. 25(5) (2005) pp. 1655-1668.
Kolodny et al., "Current Concepts in Genetics; Lysosomal Storage Disease," The New England Journal of Medicine, 294(22):1217-1220 (1976).
Komaromy, M.C. et al., "Cloning of rat hepatic lipase cDNA: Evidence for a lipase gene family," Proc. Natl. Acad. Sci. USA, vol. 84 (Mar. 1987) pp. 1526-1530.
Kostner et al., "Plasma Lipids and Lipoproteins of a Patient with Cholesteryl Ester Storage Disease," J. Inher. Metab. Dis. 8:9-12 (1985).
Kowel et al., "Low Density Lipoprotein Receptor-Related Protein Mediated Uptake of Cholesteryl Esters Derived from apoprotein E-Enriched Lipoproteins," Proc. Natl. Acad. Sci., 86:5810-5814 (1989).
Krivit et al., "Wolman Disease Successfully Treated by Bone Marrow Transplantation," Bone Marrow Transplantation, 26:567-570 (2000).

Krivit, et al., "Wolman's Disease: A Review of Treatment with Bone Marrow Transplantation and Considerations for the Future," Bone Marrow Transplantation, 1992, vol. 10, Issues Supp. 1, pp. 97-101.
Künnert et al., "Cholesteryl ester storage disease and sea-blue histiocytes," Zentralbl. Allg. Pathol. Pathol. Anat. 133:517-525 (1987).
Künnert et al., "Zur Diagnostik and Morphologic der Leber bei Cholesterolester-Speicher-krankheit," Zbl. Allg. Pathol. a. pathol. Anat. 123:71-84 (1979).
Kuntz et al., "Cholesterinester-Speicherkrankheit der Leber," Leber Magen Darm 11, Nr. 6:258-263 (1981).
Kuriwaki et al., Morphological Characteristics of Lipid Accumulation in Liver-Constituting Cells of Acid Lipase Deficiency Rats (Wolman's Disease Model Rats), Pathology International, 49:291-297 (1999).
Kuriyama, M. et al., "Lysosomal acid lipase deficiency in rats: lipid analyses and lipase activities in liver and spleen," Journal of Lipid Research, vol. 31 (1990) pp. 1605-1612.
Kyriakides, E.C. et al., "Lipid accumulation and acid lipase deficiency in fibroblasts from a family with Wolman's disease, and their apparent correction in vitro," J. Lab. Clin. Med. (Dec. 1972) pp. 810-816.
Laird et al., "Simplified Mammalian DNA Isolation Procedure," Nucleic Acids Research, 19(15):4293 (1991).
Lake et al., "Histochemical Detection of the Enzyme Deficiency in Blood Films in Wolman's Disease," J. Clin. Path., 24:617-620 (1971).
Lake et al., "Wolman's Disease Deficiency of E600-Resistant Acid Esterase Activity with Storage of Lipids in Lysosomes," The Journal of Pediatrics, 76(2):262-266 (1970).
Lanzo et al., "Fluorescence quenching analysis of the association and dissociation of a diarylheterocycle to cyclooxygenase1-1 and cyclooxygenase-2: dynamic basis of cycloxygenase-2 selectivity," Biochemistry, May 23, 2000, vol. 39(20), pp. 6228-6234.
Lashford et al., "Lysosomal Storage Disorders," Gene Therapy Technologies, Applications and Regulations, John Wiley & Sons, 1999.
Lee et al., "Intragenic Deletion as a Novel Type of Mutation in Wolman Disease," Molecular Genetics and Metabolism, 104:703-705 (2011).
Lee et al., "Mannose Receptor-Mediated Regulation of Serum Glycoprotein Homeostasis," Science, 295:1898-1901 (2002).
Leone et al., "Treatment and liver transplantation for cholesterol ester storage disease," The Journal of Pediatrics, 127(3):509-510 (1995).
Leone et al., "Use of simvastatin plus cholestyramine in the treatment of lysosomal acid lipase deficiency," The Journal of Pediatrics, 119(6):1008-1009 (1991).
Leonova et al., "Proteolytic Processing Patterns of prosaposin in Insect and Mammalian Cells," The Journal of Biological Chemistry, 271(29):17312-17320 (1996).
Leslie et al., "A Mouse Model of Galactose-1-Phosphate Uridyl Transferase Deficiency," Biochemical and Molecular Medicine, 59:7-12 (1996).
Levy et al., "Cholesteryl Ester Storage Disease: Complex Molecular Effects of Chronic Lovastatin Therapy," Journal of Lipid Research, 33:1005-1015 (1992).
Lew et al., "A Mannose Receptor Mediates Mannosyl-Rich glycoprotein-Induced Mitogenesis in Bovine Airway Smooth Muscle Cells," J. Clin. Invest., 94:1855-1863 (1994).
Li et al., "Gsh-1, An Orphan Hox Gene, is Required for Normal Pituitary Development," The EMBO Journal, 15(4):714-724 (1996).
Lian, X. et al., "Lysosomal acid lipase deficiency causes respiratory inflammation and destruction in the lung," Am. J. Physiol. Lung Cell Mol. Physiol., 2004, vol. 286, pp. L801-L807.
Liu et al., "Phenotypic Correction of Feline Lipoprotein Lipase Deficiency by Adenoviral Gene Transfer," Human Gene Therapy, 11:21-32 (2000).
Lohse et al., "Compound Heterozygosity for a Wolman Mutation is Frequent Among Patients with Cholesteryl Ester Storage Disease," Journal of Lipid Research, 41:23-31 (2000).
Lohse et al., "Human Lysosomal Acid Lipase/Cholesteryl Ester Hydrolase and Human Gastric Lipase: Identification of the Cata-

(56) References Cited

OTHER PUBLICATIONS lytically Active Serine, Aspartic Acid, and Histidine Residues," Journal of Lipid Research, 38:892-903 (1997).

Lohse et al., "Human Lysosomal Acid Lipase/Cholesteryl Ester Hydrolase and Human Gastric Lipase: Site-Directed Mutagenesis of Cys227 and Cys236 Results in Substrate-Dependent Reduction of Enzymatic Activity," Journal of Lipid Research,38:1896-1905 (1997).

Lohse et al., "Molecular Defects Underlying Wolman Disease Appear to be More Heterogeneous than those Resulting in Cholesteryl Ester Storage Disease," Journal of Lipid Research, 40:221-228 (1999).

Lohse et al., "The Acid Lipase Gene Family: Three Enzymes, One Highly Conserved Gene Structure," Journal of Lipid Research, 38:880-891 (1997).

Longhi et al., "Cholesteryl Ester Storage Disease: Risk Factors for Atherosclerosis in a 15-Year-Old Boy," J. Inher. Metab. Dis., 11(2):143-145 (1988).

Lopez, J.M. et al., "Sterol regulation of acetyl coenzyme A carboxylase: A mechanism for coordinate control of cellular lipid," Proc. Natl. Acad. Sci. USA, Feb. 1996, vol. 93, pp. 1049-1053.

Losoardo, D.W., et al. "Gene Therapy for Myocardial Angiogenesis: Initial Clinical Results with Direct Myocardial Injection of ph VEGF 165 as Sole Therapy for Myocardial Ischemia," http://www.circulationaha.org, 1998, vol. 98, pp. 2800-2804.

Lough et al., "Wolman's Disease: An Electron Microscope, Histochemical, and Biochemical Study," Arch. Path, 89:103-110 (1970).

Lowden et al., "Wolman's Disease: A Microscopic and Biochemical Study Showing Accumulation of Ceroid and Esterified Cholesterol," C.M.A. Journal, 102:402-405 (1970).

Lowe, M.E., "Cloning and Characterization of Human Pancreatic Lipase cDNA," J. Biol. Chem., vol. 264(33) (1989) pp. 20042-20048.

Lübke et al., "Proteomics of the Lysosome," Biochim Biophys Acta, 1793(4):625-635 (2009).

Ludwig, J.R. et al., "Nonalcoholic Steatohepatitis: Mayo Clinic Experiences with a Hitherto Unnamed Disease," Mayo Clinic Proc., 1980, vol. 55, pp. 434-438.

Lusa, S. et al. "Degradation of low density lipoprotein cholesterol esters by lysosomal lipase in vitro, Effect of core physical state and basis of species selectivity," Biochem. Biophy. Acta., vol. 1389 (1998) pp. 112-122.

Mao, et al., "Sortase-Mediated Protein Ligation: A New Method of Protein Engineeling." J. Am. Chem. Soc. 126, 2670-2671, 2004.

Marchesini, G. et al., "Nonalcoholic fatty liver disease: A feature of the metabolic syndrome," Diabetes, Aug. 2001, vol. 50(8), pp. 1844-1850.

Marsh et al., "Apolipoprotein B Metabolism in Humans: Studies with Stable Isotope-Labeled Amino Acid Precursors," Atherosclerosis, 162:227-244 (2002).

Marshall et al., "Wolman's Disease: A Rare Lipidosis with Adrenal Calcification," Arch. Dis. Childhood, 44:331-341 (1969).

Martinez et al., "7 Years' Experience with Hepatic Transplantation in Children," 6(1):7-10 (1993).

Maslen et al., "Occurence of a mutation associated with Wolman disease in a family with cholesteryl ester storage disease," J. Inher. Metab. Dis., 18:620-623 (1995).

Mayatepek et al., "Fatal genetic defect causing Wolman Disease," J. Inher. Metab. Dis., 22:93-94 (1999).

McCall, D. et al., "Calcium Entry Blocking Drugs: Mechanisms of Action, Experimental Studies and Clinical Uses," Year Book Medical Publishers, Inc., 1985, pp. 1-80.

McCoy et al., "Treatment of Cholesteryl Ester Storage Disease with Combined Cholestyramine and Lovastatin," Ann NY Acad. Sci., pp. 453-454 (1991).

McPhee et al., "Effects of AAV-2 mediated aspartoacylase gene transfer in the tremor rat model of Canavan disease," Molecular Brain Research, 135:112-121 (2005).

Meikle et al., "Prevalence of Lysosomal Storage Disorders," JAMA, 281(3):249-254 (1999).

Melling et al., "Localised massive tumourous xanthomatosis of the small intestine," Int. J. Colorectal Dis., 22:1401-1404 (2007).

Meyers, et al., "The use of parenteral hyperalimentation and elemental formula feeding in the treatment of Wolman disease" Nutrition Research, Dec. 1985, vol. 5, pp. 423-429.

Michels et al., "Cholesteryl Lignocerate Hydrolysis in Adrenoleukodystrophy," Pediat. Res. 14:21-23 (1980).

Michels et al., "Pulmonary vascular obstruction associated with cholesteryl ester storage disease," The Journal of Pediatrics, 94:621-622 (1979).

Mistry et al., "Therapeutic delivery of proteins to macrophages: implications for treatment of Gaucher's disease," The Lancet, 348:1555-1556 (1996).

Mitchell et al., "Cyclo-oxygenase-2: pharmacology, physiology, biochemistry and relevance to NSAID therapy," British Journal of Pharmacology, 1999, vol. 128, pp. 1121-1132.

Moran, et al., "Pathologic Gene Expression in Gaucher Diseases: Up-Regulation of Cysteine Proteinases Including Osteoclastic Cathepsin K," Blood, vol. 96(5) (Sep. 1, 2000) pp. 1969-1978.

Mori et al., "Identification of the Mannan-Binding Protein from Rat Livers as a Hepatocyte Protein Distinct from the Mannan Receptor on Sinusoidal Cells," Archives of Biochemistry and Biophysics, 222(2):542-552 (1983).

Muntoni et al., "A missense mutation (Thr-6Pro) in the lysosomal acid lipase (LAL) gene is present with a high frequency in three different ethnic populations: impact on serum lipoprotein concentrations," Hum Genet, 97:265-267 (1996).

Muntoni et al., "Homozygosity for a splice junction mutation in exon 8 of the gene encoding lysosomal acid lipase in a Spanish kindred with cholesterol ester disease (CESD)," Hum Genet, 95:491-494 (1995).

Muntoni et al., "Prevalence of Cholesteryl Ester Storage Disease," Arterioscler. Thomb. Vasc. Biol., 27:1866-1868 (2007).

Nakagawa et al., "Cloning of rat lysosomal acid lipase cDNA and identification of the mutation in the rat model of Wolman's disease," J. Lipra Res 36:2212-2213 (1995).

Negre, et al., "Lipases et Cholesterol Esterases Acides: Maladie De Wolman et Cholesteryl Ester Storage Disease (Polycorie Cholesterolique de L'Adulte)" Path Biol, 36(2), 167-181, 1988 ("Acid Lipases and Acid Cholesterol Esterases: Wolman's Disease and Cholesteryl Ester Storage Disease," Path Biol., 36(2): 167-181 (1988)).

Negre-Salvayre et al., "UV-treated lipoproteins J. Lipid Res. as a model system for the study of the biological effects of lipid peroxides on cultured cells. 4. Calcium is involved in the cytotoxicity of UV-treated LDL on lymphoid cell lines," Biochimica et Biophysica Acta, 1123:1207-215 (1992).

Neufeld, E.F. et al., "The transport of Lysosomal Enzymes," J. Supramol. Struct., vol. 6 (1977) pp. 95-101.

Nobili et al., "Treatment of nonalcoholic fatty liver disease in adults and children: a closer look at the arsenal," J Gastroenterol, (2011). DOI 10.1007/s00535-011-0467.

Noorman et al., "The mannose receptor, localization and role in the clearance of tissue-type plasminogen activator," Fibrinolysis & Proteolysis, 12(4):241-250 (1998).

Odievre, "Clinical presentation of Metabolic Liver Disease," J. Inher. Metab. Dis., 14:526-530 (1991).

Osborne, T.F. et al., "Related Membrane Domains in Proteins of Sterol Sensing and Cell Signaling Provide a Glimpse of Treasures Still Buried within the Dynamic Realm of Intracellular Metabolic Regulation," Current Opinion in Lipidology, vol. 9(2) (Apr. 1998) pp. 137-140.

Osborne, T.F., "Transcriptional Control Mechanisms in the Regulation of Cholesterol Balance," Critical Reviews in Eukaryotic Gene Expression, 1995, vol. 5(3 & 4), pp. 317-335.

Ozmen et al., "Wolman's disease: ultrasonographic and computed tomographic findings," Pediatr Radiol, 22:541-542 (1992).

Pagani et al., "A histidine to tyrosine replacement in lysosomal acid lipase causes cholesteryl ester storage disease," Human Molecular Genetics, 3(9): 1605-1609 (1994).

Pagani et al., "Expression of lysosomal acid lipase mutants detected in three patients with cholesteryl ester storage disease," Human Molecular Genetics, 5(10):1611-1617 (1996).

(56) References Cited

OTHER PUBLICATIONS

Pagani et. al, "Cysteine residues in human lysosomal acid lipase are involved in selective cholesteryl esterase activity," Biochem J. 326:265-269 (1997).
Pagani, F. et al., "New lysosomal acid lipase gene mutants explain the phenotype of Wolman disease and cholesteryl ester storage disease," Journal of Lipid Research, vol. 39 (1998) pp. 1382-1388.
Pariyarath, R. et al., "L273S missense substitution in human lysosomal acid lipase creates a new N-glycosylaton site," FEBS Letter, 1996, vol. 397 (1996) pp. 79-82.
Pastores, et al., "Enzyme Therapy for the Lysosomal Storage Disorders: Principles, Patents, Practice and Prospect," Expert Opin. Therapeutic Patients, 13(8):1157-1172 (2003).
Patrick et al., "Deficiency of an Acid Lipase in Wolman's Disease," Nature, 222:10671068 (1969).
Penning, T., "Synthesis and Biological Evaluation of the 1,5-Diarylpyrazole Class of Cyclooxygenase-2 Inhibitors: Identification of 4-[5-(4-Methylphenyl)-3-(trifluoromethyl)-1H-pyrozol-1-yl]benzenesulfonamide (SC-58635,Celecoxib)," J. Med. Chem., 1997, vol. 40(9), pp. 1347-1365.
Pentchev et al., "Incorporation of Exogenous Enzymes into Lysosomes: A Theoretical and Practical Means for Correcting Lysosomal Blockage," American Chemical Society, 150-151 (1978).
Pfeifer et al., "Cholesteryl Ester Storage Disease: Report on Four Cases," Virchows Arch. B. Cel Path. 33:17-34 (1980).
Phillipps et al., "Secretion of insulin-like growth factor-II into bile of rats of different ages," Biol Neonate, 78(2):106-12 (2000).
Pisciotta et al., "Cholesteryl Ester Storage Disease (CESD) due to novel mutations in the LIPA gene," Molecular Genetics and Metabolism, 79:143-148 (2009).
Pomerantz et al., "Boichemical Mechanisms Associated with the Lipolytic Effects of Calcium Channel Blockers," Medical Science Symposia Series, vol. 2 (1993) pp. 251-260.
Poorthuis et al., "The frequency of lysosomal storage disease in the Netherlands,"Hum genet, 105:151-156 (1999).
Poupetova et al., "LSDS with Neurologic Involvement: The birth prevalence of lysosomal storage disorders in the Czech Republic: comparison with data in different populations," J. Inherit Metab Dis, 33:387-396 (2010).
Pouton et al., "Key issues in non-viral gene delivery," Adv., Drug Deliv. Rev., vol. 46(1-3) (2001) pp. 187-203.
Powell, E.E. et al., "The Natural History of Nonalcoholic Steatohepatitis: A Follow-up Study of Forty-two Patients for Up to 21 Years," Hepatol, 1990, vol. 11, p. 74.
Poznansky, M.J. et al., "Enzyme replacement therapy in fibroblasts from a patient with cholesteryl ester storage disease," The FASEB Journal, vol. 3 (Feb. 1989) pp. 152-156.
Prowse, A.H. et al., "Somatic Inactivation of the VHL Gene in Von Hippel-Lindau Disease Tumors," Am. J. Hum. Genet., 1997, vol. 60, pp. 765-771.
Rademaker, B. et al., "Enzyme-replacement therapy: problems and prospects," Pharm. Weekly, vol. 11(5) (1989) pp. 137-145.
Rader, D., "Expression of Adenoviral Vector Containing the cDNA for Human Lysosomal Acid Lipase in Hela and Wolman Cells," Abstract 1341, FASEB Journal, Annual Meeting of Professional Research Scientists vol. 10(3) (Mar. 8, 1996).
Rader, D.J. et al., "Gene Therapy for Dyslipidemia: Clinical Prospects," Current Atherosclerosis Reports, vo. 1 (1999) pp. 58-69.
Raivio et al., "Genetic Diseases of Metabolism," Annu. Rev. Biochem 41:543-576 (1972).
Rassoul et al., "Long-term administration of the HMG-CoA reductase inhibitor lovastatin in two patients with cholesteryl ester storage disease," International Journal of Clinic Pharmacology and Therapeutics, vol. 39, No. 5:199-204 (2001).
Read et al., "Barriers to gene delivery using synthetic vectors," Adv. Genet., vol. 53 (2005) pp. 19-46.
Redonnet-Vernhet et al., "Cholesteryl Ester Storage Disease: Relationship between Molecular Defects and in Situ Activity of Lysosomal Acid Lipase," Biochemical and Molecular Medicine, 62:42-49 (1997).
Remington, The Science and Practice of Pharmacy, 19$^{th}$ Ed., Mack Publishing Co., Eaton, PA (1995) p. 963.
Ries et al., "A new mutation in the gene for lysosomal acid lipase leads to Wolman disease in an African kindred," Journal of Lipid Research, 37:1761-1762 (1996).
Ries, S. et al., "Different Missense Mutations in Histidine-108 of Lysosomal Acid Lipase Cause Cholestetyl Ester Storage Disease in Unrelated Compound Heterozygous and Hemizygous Individuals," Human Mutation, 1998, vol. 12, pp. 44-51.
Ries, S. et al., "Transcriptional regulation of lysosomal acid lipase in differentiating monocytes is mediated by transcription factors Sp1 and AP-2," Journal of Lipid Research, 1998, vol. 39, pp. 2125-2134.
Rigotti, A. et al., "A targeted mutation in the murine gene encoding the high-density lipoprotein (HDL) receptor scavenger receptor class B type I reveals its key role in HDL metabolism," Proc. Natl. Acad. Sci. USA, vol. 94 (Nov. 1997) pp. 12610-12615.
Riva et al., "Hepatocarcinoma in a child with cholesterol ester storage disease," Digestive and Liver Disease, 40:784 (2008).
Rosenbaum et al., "Thiadiazole Carbamates: Potent Inhibitors of Lysosomal Acid Lipase and Potential Neimann-Pick Type C Disease Therapeutics," J Med Chem., 53(14):52815289 (2010).
Rosengart, T. et al., "Six-Month Assessment of a Phase I Trial of Angiogenic Gene Therapy for the Treatment of Coronary Artery Disease Using Direct Intramyocardial Administration of an Adenovirus Vector Expressing the VEGF 121 cDNA", Annals of Surgery, 1999, vol. 230, No. 4, pp. 466-472.
Rosengart, T., "Angiogenesis Gene Therapy: Phase I Assessment of Direct Intramyocardial Administration of an Adenovirus Vector Expressing VEGF 121 cDNA to Individuals with Clinically Significant Severe Coronary Artery Disease," Clinical Investigation and Report, 1999, vol. 100; pp. 468-474.
Rosenthal, Nonalcoholic Fatty Liver Disease in Pediatric Patients—A Problem that is 'Enormous' and 'Growing,' JPEN J Parenter Enteral Nutr 36:7S (2012).
Rothe, G. et al., "Altered mononuclear phagocyte differentiation associated with genetic defects of the lysosomal acid lipase," Atherosclerosis, 1997, vol. 130, pp. 215-221.
Roussel et al., "Crystal Structure of Human Gastric Lipase and Model of Lysosomal Acid Lipase, Two Lipolytic Enzymes of Medical Interest," The Journal of Biological Chemistry, 274(24):16995-17002 (1999).
Röyttä et al., "Wolman disease: morphological, clinical and genetic studies on the first Scandinavian cases," Clin Genet, 42:1-7 (1992).
Rudel, L.L. et al., "Determination of cholesterol using o-phthalaldehyde," Journal of Lipid Research, 1973, vol. 14, pp. 364-366.
Russell, C.S. et al., "Recombinant proteins for genetic disease," Clin. Genet., vol. 55 (1999) pp. 389-394.
Sakai, J. et al., "Identification of Complexes Between the COOH-terminal Domains of Sterol Regulatory Element-binding Proteins (SREBPs) and SREBP Cleavage-Activating Protein," J. Biol. Chem., vol. 272(32) (Aug. 8, 1997) pp. 20213-20221.
Sakai, J. et al., "Sterol-Regulated Release of SREBP-2 from Cell Membranes Requires Two Sequential Cleavages, One Within a Transmembrane Segment," Cell, vol. 85 (Jun. 28, 1996) pp. 1037-1046.
Salvayre et al., "Maladie de Wolman et polycorie cholesterolique de l'adulte (cholesteryl ester storage disease): Nuoveaux moyens d'etude et de diagnostic," Ann. Biol. Clin. 44:611-617 (1986).
Salvetti et al., "Gene therapy of lysosomal storage disorders," British Medical Bulletin, 51(1):106-122 (1995).
Sando, G.N. "Human Lysosomal Acid Lipase/Cholesteryl Ester Hydrolase, Purification and Properties of the Form Secreted by Fibroblasts in Microcarrier Culture," The Journal of Biological Chemistry, vol. 260 (28) (Dec. 5, 1985) pp. 15186-15193.
Sando, G.N. et al., "Human Lysosomal Acid Lipase/Cholesteryl Ester Hydrolase: Purification and Properties of the Form Secreted by Fibroblasts in Microcarrier Culture," Supplement, www.jbc.org (Sep. 15, 2009) pp. 1-2.
Sando, G.N. et al., "Intercellular transport of lysosomal acid lipase mediates lipoprotein cholesteryl ester metabolism in a human vascular endothelial cell-fibroblast coculture system," Cell Regulation, vol. 1 (Aug. 1990) pp. 661-674.

(56) References Cited

OTHER PUBLICATIONS

Sando, G.N. et al., "Recognition and receptor-medicated endocytosis of the lysosomal acid lipase secreted by cultured human fibroblasts," J. Lipid Res., vol. 23 (1982) pp. 114-123.
Sanyal et al., "Endpoints and Clinical Trial Design for Nonalcoholic Steatohepatitis," Hepatology, 54(1):344-345 (2011).
Sato, R. et al., "Assignment of the Membrane Attachment, DNA Binding, and Transcriptional Activation Domains of Sterol Regulatory Element-binding Protein-1, (SREBP-1)," J. Biol. Chem., vol. 269(25) (1994) pp. 17267-17273.
Schaub et al., "Wolman's Disease: Clinical, Biochemical and Ultrastructural in an Unusual Case Without Striking Adrenal Calcification" Eur. J. Ped., 135:45-53 (1980).
Schiff et al., "Hepatic Cholesteryl Ester Storage Disease, a Familial Disorder," American Journal of Medicine, 44:538-546 (1968).
Schiffmann, R. et al., "Infusion of a-galactosidase A reduces tissue globotriaosylceramide storage in patients with Fabry disease," PNAS, vol. 97(1) (Jan. 4, 2000) pp. 365-370.
Scriver, C.R., et al, "Acid Lipase Deficiency: Wolman Disease and Cholesteryl Ester Storage Disease" Chapter 82: *The Metabolic and Molecular Bases of Inherited Disease*, 7$^{th}$ Ed., vol. II, McGraw-Hill, 1995.
Seedorf et al., "A Novel Variant of Lysosomal Acid Lipase (Lue336→Pro) Associated with Acid Lipase Deficiency and Cholesterol Ester Storage Disease," Arteriosclerosis, Thrombosis, and Vascular Biology, 15:773-778 (1995).
Sheriff et al., "Characterization of lysosomal acid lipase by site-directed mutagenesis and heterologous expression," J. Biol. Chem., vol. 270(46) (1995) pp. 27766-27772.
Shetty, K. et al., "Gene therapy of hepatic diseases: prospects for the new millennium", Gut, 2000, vol. 46, pp. 136-139.
Shimada et al., "Suppression of diet-induced atherosclerosis in low density lipoprotein receptor knockout mice overexpressing lipoprotein lipase," Proc. Natl. Acad. Sci. USA, 93:7242-7246 (1996).
Shimida, Y. et al., "cDNA Molecular Cloning of Geotrichum candidum Lipase," J. Biochem. (Tokyo), vol. 106 (1989) pp. 383-388.
Shimomura, I et al., "Cholesterol feeding reduces nuclear forms of sterol regulatory element binding proteins in hamster liver," Proc. Natl. Acad. Sci. USA, Nov. 1997, vol. 94, pp. 12354-12359.
Shome et al., "The Middle-East Connection of Wolman Disease," Saudi. Med. J., 23(5):597-601 (2002).
Sigma-Aldrich, "Sigma Chemical Company product sheet for the Pseudomonas-derived cholesterol esterase" www.sigmaaldrich.com, 2010.
Skinner et al., "Cholesterol Curves to Identify Norms by Age and Sex in Healthy Weight Children," Clin Pediatr, 51:233 (2012).
Sloan et al., "Enzyme Deficiency in Cholesteryl Ester Storage Disease," the Journal of Clinical Investigation, 51:1923-1924 (1972).
Sly et al., "Enzyme therapy in mannose receptor-null mucopolysaccharidosis VII mice defines roles for the mannose 6-phosphate and mannose receptors," PNAS, 103(41):15172-15177 (2006).
Smith, et al., "Peptide Sequences Mediating Tropism to Intact Blood-Brain Barrier: An In Vivo Biodistribution Study Using Phage Display," Peptides, 38:172-180 (2012).
Somerharju, P.L.S., "Degradation of low density lipoprotein cholesterol esters by lysosomal lipase in vitro. Effect of core physical state and basis of species selectivity," Biochim. Biophys. Acta., Jan. 15, 1998, vol. 1389(2), pp. 112-122 [Abstract].
Soyombo et al., "TRP-ML1 regulates lysosomal pH and acidic lysosomal lipid hydrolytic activity," J. Biol. Chem., vol. 281(11) (2006) pp. 7294-7301.
Spiegel-Adolf et al., "Hematologic Studies in Niemann-Pick and Wolman's Disease." Confin. Neurol, 28:399-406 (1966).
Stahl et al., "Evidence for receptor-mediated binding of glycoproteins, glycoconjugates, and lysosomal gylcosidases by alveolar macrophages," Cell Biology, 75(3):1399-1403 (1978).
Stein, et al., "Successful Treatment of Wolman Disease by Unrelated Umbilical Cord Blood Transplantation," Europ. J. Pediatrics 166(7):663-666 (2007).
Sternby et al., "Carboxyl Ester Lipase (Bile Salt-Stimulated Lipase), Colipase, Lipase, and Phospholipase A2 Levels in Pancreatic Enzyme Supplements," Scand J Gastroenterol 32:261-267 (1997).
Surve et al., "Wolman Disease: Diagnosis by Leucocyte Acid Lipase Estimation," Indian Journal of Pediatrics, 72:353-354 (2005).
Suzuki et al., "Are animal models useful for understanding the pathophysiology of lysosomal storage disease?" Acta Paediatr Suppl, 443:54-62 (2003).
Swinnen, J.V. et al., "Coordinate regulation of lipogenic gene expression by androgens: Evidence for a cascade mechanism involving sterol regulatory element binding proteins," Proc. Natl. Acad. Sci. USA, Nov. 1997, vol. 94, pp. 12975-12980.
Tadiboyina, "Treatment of dyslipidemia with lovastatin and ezetimibe in an adolescent with cholesterol ester storage disease," Lipids in Health and Disease, 2005, vol. 4, Issue 26, pp. 1-6.
Takahashi et al., "Distribution of murine mannose receptor expression from early embryogenesis through to adulthood," Cell Tissue Res 292:311-323 (1998).
Takasaki et al., "Structure of the N-Asparagine-linked Oligosaccharide Units of Human Placental β-Glucocerebrosidase," The Journal of Biological Chemistry, 259(16):1011210117 (1984).
Talley et al., "4[5-Methyl-3-[phenylisoxazol-1-yl]benzenesulfonamide, Valdecoxib: A Potent and Selective Inhibitor of COX-2," J. Med. Chem., 2000, vol. 43, pp. 775-777.
Talley et al., "N-[[(5-methyl-3-phenylixoxazol-4yl)-phenyl]sulfonyl]propanimide, Sodium Salt, Parecoxib Sodium: A Potent and Selective Inhibitor of COX-2 for Parenteral Administration," J. Med. Chem., 2000, vol. 43, pp. 1661-1663.
Talley, J. et al., "4,5-Diaryloxazole inhibitors of cyclooxygenase-2 (COX-2)," Med. Res. Rev., May 1999, vol. 19(3), pp. 199-208.
Tanaka et al., Acid Lipase Deficiency: Wolman Disease and Cholesteryl Ester Storage Disease, Nippon Rinsho, 53(12):3004-3008 (1995).
Tarantino et al., "Lovastatin therapy for cholesterol ester storage disease in two sisters," The Journal of Ped., 118(1):131-135 (1991).
Temel, R.E. et al., "Scavenger receptor class B, type I (SR-BI) is the major route for the delivery of high density lipoprotein cholesterol to the steroidogenic pathway in cultured mouse adrenocortical cells," Proc. Natl. Acad. Sci. USA, vol. 94 (1997) pp. 13600-13605.
Thavarungkul et al., "Cholesterol Ester Storage Disease: A Reported Case," J. Med. Assoc. Tha; 78(3):165-165.
Thompson et al., "Role of cholesterol in regulating apolipoprotein B secretion by the liver," Journal of Lipid Research, 37:439-440 (1996).
Tietge et al., "Phenotypic Correction of Lipid Storage and Growth Arrest in Wolman Disease Fibroblasts by Gene Transfer of Lysosomal Acid Lipase," Human Gene Therapy, (Feb. 10, 2001) pp. 279-289.
Todoroki et al., "Accumulated lipids, aberrant fatty acid composition and defective cholesterol ester hydrolase activity in cholesterol ester storage disease," Ann Clin Biochem, 37:187-193 (2000).
Tolar et al., "Long-term metabolic, endocrine, and neuropsychological outcome of hematopoietic cell transplantation for Wolman disease," Bone Marrow Transplantation, 43:21-27 (2009).
Tontonoz, P. et al., "ADD1: a Novel Helix-Loop-Helix Transcription Factor Associated with Adipocyte Determination and Differentiation," Molecular and Cellular Biology, Aug. 1993, vol. 13, No. 8, pp. 4753-4759.
Tylki-Szymahska et al, "Clinical, biochemical and histological analysis of seven patients with cholesteryl ester storage disease," Acta Paediatrica Japonica, 39:643-646 (1997).
Uniyal et al., "Wolman's Disease," Indian Pediatrics, 32:232-233 (1994).
Updike, S.J., "Genetic Engineering, Enzyme Immobilization, and Transplantation," American Journal of Pharmaceutical Education, 1972, vol. 78, pp. 718-722.
Van Berkel, "The role of non-parenchymal cells in liver metabolism," TIBS 202-205, Sep. 1979.
Van Erum et al., "Cholesteryl Ester Storage Disease with Secondary Lecithin Cholesterol Acyl Transferase Deficiency," J. Inher. Metab. Dis 11 Suppl. 2:146-148 (1988).
Varki et al., "Studies of synthesis, structure and function of the phosphorylated oligosaccharides of lysosomal enzymes," J. Biosci, 5(1):101-104 (1983).

(56) References Cited

OTHER PUBLICATIONS

Vogler, et al., "Enzyme Replacement With Recombinant B-Glucuronidase in Murine Mucopolysaccharidosis Type VII: Impact of Therapy During the First Six Weeks of Life on Subsequent Lysosomal Storage, Growth, and Survival," Pediatr Res. 39(6), 1996, pp. 1050-1054.
Vom Dahl et al., "Lysosomal storage disease as differential diagnosis of hepatosplenomegaly," Best Practice & Research Clinical Gastroenterology, 24:619-628 (2010).
Von Figura et al., "Lysosomal Enzymes and Their Receptors," Ann. Rev. Biochem, 55:167-193 (1986).
Von Trotha, K.-T, et al., "Influence of Lysosomal Acid Lipase Polymorphisms on Chromosome 10 on the Risk of Alzheimer's Disease and Cholesterol Metabolism," Neuroscience Letters, 402(3):262-266 (2006) (Abstract only).
Vuillemenot et al., "Intrathecal tripeptidyl-peptidase 1 reduces lysosomal storage in a canine model of late infantile neuronal ceroid lipofuscinosis," Molecular Genetics and Metabolism, 104:325-337 (2011).
Walters et al., "Cholesterol esterase activities in commercial pancreatic enzyme preparations and implications for use in pancreatic insufficient cystic fibrosis," Journal of Clinical Pharmacy and Therapeutics, 26:425-431 (2001).
Walters, et al., "Calcium Channel Blockers and Coronary Atherosclerosis: From the Rabbit to the Real World," American Heart Journal, vol. 128(6) 11 Suppl. (1994) pp. 1309-1316.
Wang, X. et al., "Nuclear Protein That Binds Sterol Regulatory Element of Low Density Lipoprotein Receptor Promoter," The Journal of Biological Chemistry, 1993, vol. 268, pp. 14497-14504.
Wang, X. et al., "SREBP-1, a Membrane-Bound Transcription Factor Released by Sterol-Regulated Proteolysis," Cell, vol. 77 (Apr. 8, 1994) pp. 53-62.
Warner et al., "Purification of the Lysosomal Acid Lipase from Human Liver and Its Role in Lysosomal Lipid Hydorlysis," The Journal of Biological Chemistry, 246(6):2952-2957 (1981).
Warner et al., "Separation and Characterization of the Acid Lipase and Neutral Esterases from Human Liver," Am. J. Hum Genet, 32:869-879 (1980).
Warner, G.J., et al., "Cell Toxicity Induced by Inhibition of Acyl Coenzyme A: Cholesterol Acyltransferase and Accumulation of Unesterified Cholesterol," The Journal of Biological Chemistry, Mar. 17, 1995, vol. 170, No. 11, pp. 5772-5778.
Wert, S.E. et al., "Increased metalloproteinase activity, oxidant production, and emphysema in surfactant protein D gene-inactivated mice," Proc. Natl. Acad. Sci USA, May 23, 2000, vol. 97, No. 11, pp. 5972-5977.
Wolf, "The mechanism and regulation of fat mobilization from adipose tissue: desnutrin, a newly discovered lipolytic enzyme," Nutr. Rev., vol. 63(5) (May 2005) pp. 166-170.
Wolman, "Involvement of Nervous Tissue in Primary Familial Xanthosmatosis with Adrenal Calcification," Path Europe, 3:259-265 (1968).
Wolman, "Primary Familial Xanthomatosis with Involvement and Calcification of the Adrenals: Report of Two or More Cases in Siblings of a Previously Described Infant," Pediatrics, 28:742-757 (1961).
Wolman, "Proposed Treatment for Infants with Wolman Disease," Pediatrics, 83:10741075 (1989).
Wolman, et al., "Wolman Disease and Its Treatment," Clin. Pediatr. 34(4):207-212 (1995).
Wong, et al., Nonpeptide Angiotensin II Receptor Antagonists. 1. Pharmacological Characterization of 2-n-Butyl-4-chloro-1-(2-chlorobenzyl)imidazole-5-acetic acid, sodium salt(S-8307), The Journal of Pharmacology and Experimental Therapeutics, 1988, vol. 247(1), pp. 1-7.
XU, Y-H et al., "Turnover and Distribution of Intravenously Administered Mannose-Terminated Human Acid [beta]-Glucosidase in Murine and Human Tissues," Pediatric Research, Feb. 1996, vol. 39, Issue 2, pp. 313-322.
Yagyu et al, "Overexpressed lipoprotein lipase protects against atherosclerosis in apolipoprotein E knockout mice," Journal of Lipid research, 40:1677:1678 (1999).
Yan et al., "Macrophage-Specific Expression of Human Lysosomal Acid Lipase Corrects Inflammation and Pathogenic Phenotypes in lal$^{-/-}$Mice," The American Journal of Pathology, 169(3):916-917 (2006).
Yatsu et al., "Wolman Disease," Molecular and Genetic Basis of Neurological Disease. $2^{nd}$ Ed., Rosenberg, R.N., Butterworth-Heinemann (1997) pp. 371-378.
Yergey et al., "In Vitro Metabolism of the Cox-2 Inhibitor DFU, including a Novel Glutathione Adduct Rearomatization," Drug Metabolism and Disposition, May 2001, vol. 29, No. 5, pp. 638-644.
Yokoyama et al., "Long-term treatment of a homozygous cholesteryl ester storage disease with combined cholestryamine and lovastatin," J. Inher. Metab. Dis. 15:219-292 (1992).
Yokoyama, C. et al., "SREBP-1, a Basic-Helix-Loop-Helix-Leucine Zipper Protein That Controls Transcription of the Low-Density Lipoprotein Receptor Gene," Cell, vol. 75 (Oct. 8, 1993) pp. 187-197.
Yoshida, et al., "Genetic lipid storage disease with lysosomal acid lipase deficiency in rats," Lab Anim Sci., 40:486-489 (1990).
Young et al., "Deficiency of Acid Esterase Activity in Wolman's Disease," Archives of Disease in Childhood, 45:664-665 (1970).
Yu et al., "Boosting Brain Uptake of a Therapeutic Antibody by Reducing Its Affinity for a Transcytosis Target," Sci Transl Med, 3:84ra44 (2011).
Zhang et al., "Biotherapeutic target or sink: analysis of the macrophage mannose receptor tissue distribution in murine models of lysosomal storage diseases," J. Inherit Metab Disl 34:795-809 (2011).
Zhao et al., "Significant Inhibition by the Flavonoid Antioxidant Silymarin against 12-O-tetracecanoylphorbol 13-acetate-caused modulation of antioxidant and inflammatory enzymes, and cyclooxygenase 2 and interleukin-1 alpha expression in SENCAR mouse epidermis: implications in the prevention of stage I tumor promotion," Molecular Carcinogensis, Dec. 1999, vol. 26(4), pp. 321-333.
Zschenker et al., "Characterization of lysosomal acid lipase mutations in the signal peptide and mature polypeptide regions causing Wolman disease," Journal of Lipid Research 42:1033-1040 (2001).
Zschenker et al., "Lysosomal acid lipase as a preproprotein," J. Biodchem, vol. 136(1) (2004) pp. 65-72.
Zschenker et al., "Systematic Mutagenesis of Potential glycosylation Sites of Lysosomal Acid Lipase," J. Biochem., 137:387-394 (2005).
Zuliani et al., "Characterization of a New Form of Inherited Hypercholesterolemia: Familial Recessive Hypercholesterolemia," Arterioscler Throm Vasc Biol, 19:802-809 (1999).
Brazilian Opposition "Supportive Data to Examination" dated 2012 for Application No. PI 0108077-6, 27 pgs.
European Examination Report dated Feb. 19, 2004 for Application No. EP 01 906 927.
European Examination Report dated Jun. 1, 2005 for Application No. EP 01 906 927.
European Examination Report dated Oct. 5, 2007 for Application No. EP 01 906 927.
European Notice of Opposition dated Jan. 25, 2010 for Opposition against EP 1 267 917.
European Patent Application File History dated Sep. 23, 2010 for Application No. EP 01906927.7.
EPO, Reply to Communication PCT/IPEA/408, dated Feb. 1, 2002, for International Application No. PCT/US01/03481.
EPO, Annex to the Communication, dated Feb. 19, 2004. For European Application No. 01 906 927.7.
EPO, Reply to Communication for the Examining Division, dated Aug. 26, 2004, for European Application No. 01 906 927.7.
EPO, Annex to the Communication, dated Jun. 1, 2005, for European Application No. 01 906 927.7.
EPO, Reply Communication from the Examining Division, dated Oct. 4, 2005, for European Application No. 01 906 927.7.
EPO, Annex to the Communication, dated Oct. 5, 2007, for European Application No. 01 906 927.7.
EPO, Reply to Communication from the Examining Division, dated Feb. 14, 2008, for European Application No. 01 906 927.7.

(56) References Cited

OTHER PUBLICATIONS

EPO, Opposition Submission 1, of EP 1 267 914, from EP Application No. 01 906 927.7, against Children's Hospital Research Foundation, by Albrecht Dehmel, pp. 1-56, Jan. 25, 2010.
EPO, Reply of the Patent Proprietor to the Notice of Opposition, dated Sep. 15, 2010, for European Patent No. 1 267 914 / 01 906 927.7.
EPO, Letter regarding the Opposition Procedure, dated Jan. 21, 2011, for European Patent No. 1 267 914 / 01 906 927.7.
EPO, Letter regarding the Opposition Procedure, dated Jan. 24, 2011, for European Patent No. 1 267 914 / 01 906 927.7.
EPO, Opposition Submission 2, of EP 1 267 914, from EP Application No. 01 906 927.7, against Children's Hospital Research Foundation, by Albrecht Dehmel, pp. 1-17, Apr. 4, 2011.
EPO, Opposition Submission 3, of EP 1 267 914, from EP Application No. 01 906 927.7, against Children's Hospital Research Foundation, by Albrecht Dehmel, pp. 1-8, Aug. 22, 2011.
EPO, Letter regarding the opposition procedure, Further Submissions by the Opponent, dated May 21, 2012, for European Patent No. 1 267 914.
EPO, Annex to a Communication, opposition, dated May 30, 2012, for European Application No. 01 906 927.7.
EPO, Written submission in preparation for Oral Proceedings, dated Jun. 13, 2012, for European Patent No. 1 267 914.
EPO, Written submission in preparation for Oral Proceedings, dated Sep. 21, 2012, for European Patent No. 1 267 914.
EPO, Minutes of the Oral Proceedings, Opposition Division, Conclusion of the Proceedings, dated Nov. 23, 2012, for European Application No. 01 906 927.7.
EPO, Decision of the Opposition Division and Instruction, dated Dec. 10, 2012 for European Application No. 01 906 927.7, Patent No. EP-B-1 267 914.
EPO, Interlocutory Decision in Opposition Proceedings, dated Jan. 3, 2013 for European Application and Patent No. 01 906 927.7 / 1 267 914.
EPO, Annex to the Opposition Communication, dated Jan. 3, 2013 for European Application No. 01 906 927.7.
EPO, Annex to the Grounds for the Decision of the Opposition, dated Jan. 3, 2013 for European Application No. 01 906 927.7.
EPO, Annex to a Communication, opposition procedure, Citation Sheet, dated Jan. 3, 2013 for European Application No. 01 906 927.7.
EPO, Notice of Appeal of the Decision of the Opposition Division, by Albrecht Dehmel, dated Feb. 21, 2013 for European Patent No. EP 1 267 914.
French Patents Court, Grounds of Invalidity, Claim No. HC 12 C00211, between Synageva Biopharma Corp. and Children's Hospital Research Foundation, filed Jan. 16, 2012.
French Request for Service Abroad of Judicial or Extrajudicial Documents (dossier: Cor:7805, MD:73249), Jul. 9, 2012.
French Request for Service Abroad of Judicial or Extrajudicial Documents (dossier: Cor:7805, MD:73250), Jul. 9, 2012.
French Request for Service Abroad of Judicial or Extrajudicial Documents (dossier: Cor:7805, MD:73251), Jul. 9, 2012.
French Patents Court, Statement of Opposition, Claim No. HC 12 C00211, between Synageva Biopharma Corp. and Children's Hospital Research Foundation, served Feb. 13, 2013.
French Patents Court, Amended Grounds of Invalidity, Claim No. HC 12 C00211, between Synageva Biopharma Corp. and Children's Hospital Research Foundation, filed Mar. 8, 2013.
High Court of Paris, Pleadings No. 1, Docket No. 12/13131, Docket No. 12/13131, between Synageva Biopharma Corp. and Children's Hospital Research Foundation, Mar. 26, 2013.
High Court of Paris, Conclusions de Desistement D'Instance (Conclusions of Discontinuance of Proceedings), Docket No. 12/13131, between Synageva Biopharma Corp. and Children's Hospital Research Foundation, 2013.
International Search Report dated Jun. 22, 2001 for Application No. PCT/US01/03481.
International Written Opinion dated Nov. 5, 2001 for Application No. PCT/US2001/03481.
International Preliminary Examination Report dated Jun. 7, 2002 for PCT/US01/03481.
International Search Report dated Nov. 16, 2007 for Application No. PCT/US2006/034044.
International Preliminary Report on Patentability and Written Opinion dated Mar. 11, 2008 for Application No. PCT/US2006/034044.
International Search Report dated Feb. 2, 2012 for Application No. PCT/US2011/051096.
International Search Report dated Jun. 6, 2012 for Application No. PCT/US2012/025233.
International Written Opinion dated Jun. 6, 2012 for Application No. PCT/US2012/025233.
USPTO, Non-Final Office Action dated Oct. 30, 2001 for U.S. Appl. No. 09/775,517.
USPTO, Response to Non-Final Office Action dated Feb. 20, 2002 for U.S. Appl. No. 09/775,517.
USPTO, Restriction Requirement dated May 7, 2002 for U.S. Appl. No. 09/775,517.
USPTO, Restriction Requirement dated Dec. 10, 2002 for U.S. Appl. No. 09/775,517.
USPTO, Non-Final Office Action dated Apr. 1, 2003 for U.S. Appl. No. 09/775,517.
USPTO, Response to Non-Final Office Action dated Sep. 9, 2003 for U.S. Appl. No. 09/775,517.
USPTO, Final Office Action dated Oct. 30, 2003 for U.S. Appl. No. 09/775,517.
USPTO, Response to Final Office Action dated Jan. 28, 2004 for U.S. Appl. No. 09/775,517.
USPTO, Advisory Action dated Mar. 1, 2004 for U.S. Appl. No. 09/775,517.
USPTO, Notice of Appeal dated Mar. 18, 2004 for U.S. Appl. No. 09/775,517.
USPTO, Second Response to Final Office Action dated Apr. 19, 2004 for U.S. Appl. No. 09/775,517.
USPTO, Notice of Allowance dated Jun. 1, 2004 for U.S. Appl. No. 09/775,517.
USPTO, Restriction Requirement dated Nov. 15, 2006 for U.S. Appl. No. 10/776,797.
USPTO, Response to Restriction Requirement dated Jan. 19, 2007 for U.S. Appl. No. 10/776,797.
USPTO, Non-Final Office Action dated Mar. 7, 2007 for U.S. Appl. No. 10/776,797.
USPTO, Response to Non-Final Office Action dated Aug. 7, 2007 for U.S. Appl. No. 10/776,797.
USPTO, Non-Final Office Action dated Aug. 21, 2007 for U.S. Appl. No. 10/776,797.
USPTO, Response to Non-Final Office Action dated Sep. 12, 2007 for U.S. Appl. No. 10/776,797.
USPTO, Final Office Action dated Nov. 21, 2007 for U.S. Appl. No. 10/776,797.
USPTO, Response to Final Office Action dated May 21, 2008 for U.S. Appl. No. 10/776,797.
USPTO, Non-Final Office Action dated Aug. 5, 2008 for U.S. Appl. No. 10/776,797.
USPTO, Response to Non-Final Office Action dated Feb. 5, 2009 for U.S. Appl. No. 10/776,797.
USPTO, Final Office Action dated Jul. 7, 2009 for U.S. Appl. No. 10/776,797.
USPTO, Restriction Requirement dated Apr. 2, 2009 for U.S. Appl. No. 11/653,147.
USPTO, Response to Restriction Requirement dated May 1, 2009 for U.S. Appl. No. 11/653,147.
USPTO, Non-Final Office Action dated Jul. 24, 2009 for U.S. Appl. No. 11/653,147.
USPTO, Amendment and Response dated Jan. 25, 2010 for U.S. Appl. No. 11/653,147.
USPTO, Restriction/Election Requirement dated Apr. 22, 2010 for U.S. Appl. No. 11/653,147.
USPTO, Response to Restriction/Election Requirement dated Jun. 14, 2010 for U.S. Appl. No. 11/653,147.

(56) References Cited

OTHER PUBLICATIONS

USPTO, Examiner Interview Summary dated Jun. 18, 2010 for U.S. Appl. No. 11/653,147.
USPTO, Recordation of Interview Summary dated Jun. 24, 2010 for U.S. Appl. No. 11/653,147.
USPTO, Final Office Action dated Sep. 3, 2010 for U.S. Appl. No. 11/653,147.
USPTO, Examiner Interview Summary dated Feb. 16, 2011 for U.S. Appl. No. 11/653,147.
USPTO, Amendment and Response filed with RCE dated Mar. 1, 2011 for U.S. Appl. No. 11/653,147.
USPTO, Restriction/Election Requirement dated Apr. 19, 2012 for U.S. Appl. No. 11/653,147.
USPTO, Amendment and Response dated May 15, 2012 for U.S. Appl. No. 11/653,147.
USPTO, Non-Final Office Action dated Jul. 5, 2012 for U.S. Appl. No. 11/653,147.
USPTO, Applicant Initiated Interview Summary dated Oct. 11, 2012 for U.S. Appl. No. 11/653,147.
USPTO, Amendment and Response dated Jan. 3, 2013 for U.S. Appl. No. 11/653,147.
USPTO, Applicant Initiated Interview Summary dated Jan. 7, 2013 for U.S. Appl. No. 11/653,147.
USPTO, Response to Applicant Initiated Interview Summary dated Jan. 16, 2013 for U.S. Appl. No. 11/653,147.
USPTO, Final Office Action dated Feb. 19, 2013 for U.S. Appl. No. 11/653,147.
USPTO, Applicant Initiated Interview Summary dated Mar. 5, 2013 for U.S. Appl. No. 11/653,147.
USPTO, Amendment and Response dated Mar. 25, 2013 for U.S. Appl. No. 11/653,147.
USPTO, Restriction Requirement dated Aug. 17, 2010 for U.S. Appl. No. 12/065,975.
USPTO, Response to Restriction Requirement dated Sep. 14, 2010 for U.S. Appl. No. 12/065,975.
USPTO, Non-Final Office Action dated Nov. 9, 2010 for U.S. Appl. No. 12/065,975.
USPTO, Response to Non-Final Office Action dated Feb. 8, 2011 for U.S. Appl. No. 12/065,975.
USPTO, Final Office Action dated Apr. 29, 2011 for U.S. Appl. No. 12/065,975.
USPTO, Response to Final Office Action dated Aug. 24, 2011 for U.S. Appl. No. 12/065,975.
U.S. Appl. No. 15/492,650, filed Apr. 20, 2017.
U.S. Appl. No. 60/180,362, filed Feb. 4, 2000.
Gennaro, A.R., Ed., *Remington's Pharmaceutical Sciences*, 18$^{th}$ Ed., Mack Publ. Co., Easton, PA, 1990, 8 pgs.

\* cited by examiner

LIPID HYDROLYSIS THERAPY FOR ATHEROSCLEROSIS AND RELATED DISEASES

This continuation application is based on and claims priority from U.S. Non-Provisional patent application Ser. No. 12/683,265, filed Jan. 6, 2010, which continuation application is based on and claims priority from U.S. Non-Provisional patent application Ser. No. 10/776,797, filed Feb. 11, 2004, now abandoned; which is a divisional of U.S. Non-Provisional patent application Ser. No. 09/775,517, filed Feb. 2, 2001, now patented as U.S. Pat. No. 6,849,257; and U.S. Provisional Patent Application Ser. No. 60/180,362, Gregory A. Grabowski and Hong Du, filed Feb. 4, 2000.

FIELD OF INVENTION

The present invention relates to the use of lipid dissolving substances for the treatment and prevention of coronary artery disease. More specifically, this invention relates to the use of lipid hydrolyzing proteins and/or polypeptides, such as lysosomal acid lipase (LAL), for the treatment and prevention of atherosclerosis in mammals.

BACKGROUND

The increasing number of patients suffering from atherosclerosis continues to drive research into cholesterol and triglyceride metabolism. Through a large number of investigations, the essentials of the control of cholesterol metabolism have been elucidated in the past two decades (see FIG. 1). The central system for the control of cholesterol metabolism requires two sets of separable pathways: 1) the endogenous pathway and 2) the exogenous cholesterol-entry pathways. Both of sets of pathways are modulated by the protein lysosomal acid lipase (LAL) [1]. In the former, the cell senses the need for endogenous cholesterol synthesis via the release of transcription factors, Sterol Regulatory Element Binding Proteins (SREBP1 and 2), whose precursors are bound to the nuclear membrane and endoplasmic reticulum. SREBPs up-regulate HMG-CoA reductase and other enzymes in the endogenous synthesis pathways [2-5]. This upregulation is derived from the cell's biochemical feedback mechanism sensing a low level of free cholesterol in the surrounding media and/or plasma that is derived from the receptor mediated endocytosis pathway; i.e., the exogenous pathway [6]. Low density lipoprotein receptors (LDLR) and other plasma membrane receptors participate in this uptake process. These LDLR-delivered and other lipoprotein associated lipids are presented to the lysosome for degradation by LAL. Once a deficient exogenous cholesterol supply is sensed, SREBP 1 and 2 stimulate the transcription of a cascade of enzymes leading to the production of free intracellular cholesterol and fatty acids [7-10]. The cell then senses the adequacy of free cholesterol levels and, once exceeded, ACAT (acyl CoA: cholesterol acyltransferase) is directly activated by free cholesterol and ACAT synthesis is up regulated. The net effect is to remove free cholesterol by esterification to a cytoplasmic storage pool of cholesteryl esters that is not contained within membranes, i.e., non-lysosomal, and to remove free cholesterol and cholesteryl esters from the cells. Once the cell senses that sufficient free cholesterol is available, a steady state pool of free cholesterol is maintained [11].

Both SREBP 1 and 2 are transcription factors that bind to Sterol Regulatory Elements (SREs) in the promoter regions of key genes in cholesterol and fatty acid synthesis. The SREBPs are activated by a two step proteolytic process that is mediated by proteases that are activated by free cholesterol sensing elements in the plasma membrane and, potentially, other components of the cell [12, 13]. These proteases cleave the endoplasmic recticulum (ER) resident SREBPs and release their active components which are then transported to the nucleus. SREBP 2 has a single transcript whereas the SREBP-1 gene produces two transcripts and proteins, SREBP-1a and SREBP-1c. These alternative forms of SREBP 1 arise from the use of transcription start sites resident in alternative first exons that are then spliced into a common second exon. In humans, the mRNAs for SREBP-1a/-1c also display alternative splicing at the 3' end that leads to proteins that differ by 113 amino acids at the C-terminus 114, 151. All three SREBP members share the same structural domains indicating their common function [16]. These domains include: 1) the $NH_2$-terminal segment of 480 amino acids is a basic helix-loop-helix-leucine zipper-"like" transcription activator, 2) the middle segment of 80 amino acids comprises two membrane spanning sequences, and 3) the carboxy-terminal half of 590 amino acids that functions as a regulatory domain [17].

There are at least two pathways for the entrance of external cholesterol into monocyte/macrophage derived cells [18]: 1) the ldlr and ldlr-related protein systems [19]; and 2) the scavenger receptor system (e.g., SRA, SR-B and CD36) for lipoprotein bound cholesteryl esters (CE's) [20-24]. The SR-B1 pathway delivers cholesteryl esters into the cell via transfer of cholesteryl esters through SR-B1 without uptake of HDL [25, 26].

In the LDL-CE (cholesteryl ester) or -TG (triglyceride) pathway, the complexes arc taken up into cells following receptor-mediated recognition. The endosomal pathway delivers these lipids to the lysosomes after uncoupling the LDL-lipid complexes from the receptor in the late endosomal acidified compartment. Once the LDL-lipid particle is delivered to the lysosome, the lipids are liberated, possible after degradation of the LDL particle, via proteolysis or by simultaneous attack through proteolysis and by LAL [27]. This derived free cholesterol is then transported out of the lysosome into the cytosol by one or more proteins resident in, or at, the lysosomal membrane: Once it exits the lysosome, free cholesterol moves to the inner surface of the plasma membrane and directly to the endoplasmic reticulum, Free cholesterol from the inner surface of the plasma membrane is then transported to the endoplasmic reticulum and participates in the feedback control of the endogenous synthetic pathway. Thus, from this simplified overview of cholesterol and triglyceride metabolism in cells, it is clear that LAL occupies a central position in the control of endogenous cholesterol synthesis since, without its activity, neither free cholesterol nor free fatty acids (FFA) derived from the LDL pathway can be liberated from the lysosome to control these critical pathways.

The importance of LAL in cholesterol and triglyceride metabolism is underscored by the human phenotypes resulting from inherited deficiencies of LAL. These two rare diseases, Wolman Disease and Cholesteryl Ester Storage Disease, are early and late onset diseases, respectively [28]. Wolman disease results in the massive accumulation of cholesteryl esters and triglycerides in lysosomes of a variety of tissues and cells including those of the liver (hepatocytes and Kupffer cells), spleen, adrenal gland and epithelium of the small intestine. This leads to a severe phenotype characterized by hepatosplenomegaly, adrenal calcification, and a thickened and dilated small intestine. In comparison, cholesteryl ester storage disease is a much more heterogeneous disease with onset from early childhood to late adolescence, and even adulthood with isolated hepatomegaly and/or progressive cirrhosis and primarily storage of cholesteryl esters.

The inventor has discovered that additional circumstantial evidence has implicated lower LAL activities in monocytes and/or plaques from patients with atherosclerosis or carotid artery atheromata. This evidence indicates that polymorphic variants could lead to differential activity of LAL in various tissues and may predispose to, or be an additional risk factor in, the development of atherosclerotic disease in humans [29]. In accordance with this invention, this suggests that supplementation of LAL activity in cells of pathologic involvement in athero-/arterio-sclerosis may provide a means to diminish the accumulated, pathologic cholesteryl esters and triglycerides that are causally related to these diseases.

SUMMARY OF THE INVENTION

As described herein, the present invention comprises a method to diminish and/or eliminate atherosclerotic plaques in mammals, through direct and indirect treatment of these plaques, in situ, using proteins and/or polypeptides. These proteins and/or polypeptides are capable of lipid removal, primarily through hydrolysis, either by a catalytic or stoichiometric process, wherein the lipid hydrolyzing protein or polypeptide targets receptors in and/or on the cell leading to uptake into the lysosome. Receptor sites are selected from the group consisting of oligosaccharide recognition receptors and peptide sequence recognition receptors.

Generally, compositions used for practicing this invention include lipid hydrolyzing proteins or polypeptides, and in particular, the protein lysosomal acid lipase (LAL). However, other lipid hydrolyzing proteins or polypeptides may also be used, such as proteins which show at least 85% sequence homology to lysosomal acid lipase or proteins having a $Ser^{153}$ residue. Other proteins include polymorphic variants of lysosomal acid lipase with substitution of amino acid Pro(-6) to Thr and Gly2 to Arg and also polypeptides showing similar biological activity as lysosomal acid lipase.

Exogenously produced lipid hydrolyzing proteins or polypeptides, contained in a pharmaceutically acceptable carrier, may be administered either orally, parenterally, by injection, intravenous infusion, inhalation, controlled dosage release or by intraperitoneal administration in order to diminish and/or eliminate atherosclerotic plaques. The preferred method of administration is by intravenous infusion.

Endogenously produced lipid hydrolyzing proteins and/or polypeptides may also be used to diminish and/or eliminate atherosclerotic plaques. Generally, such a method involves providing a biologically active human lipid hydrolyzing protein or polypeptide, such as human lysosomal acid lipase, to cells of an individual having a deficiency in biologically active human lipid hydrolyzing protein(s) or polypeptide(s). This is accomplished by in vivo administration into cells competent for the production of biologically active human lipid hydrolyzing protein or polypeptide, a vector comprising and expressing a DNA sequence encoding biologically active human lipid hydrolyzing protein or polypeptide. The vector used may be a viral vector, including but not limited to a lentivirus, adenovirus, adeno-associated virus and virus-like vectors, a plasmid, or a lipid vesicle. The vector is taken up by the cells competent for the production of biologically active human lipid hydrolyzing protein or polypeptide. The DNA sequence is expressed and the biologically active human lipid hydrolyzing protein or polypeptide is produced. Additionally, the cells harboring this vector will secrete this biologically active lipid hydrolyzing protein or polypeptide which is then subsequently taken up by other cells deficient in the lipid hydrolyzing protein or polypeptide.

Other proteins and/or polypeptides which may be used for endogenous treatment of atherosclerotic plaques includes biologically active proteins having at least 85% sequence homology to lysosomal acid lipase, polymorphic variant proteins of lysosomal acid lipase with substitution of amino acid Pro(-6) to Thr and Gly2 to Arg and polypeptides showing similar biological activity to lysosomal acid lipase.

100151 The abbreviations for cellular components are as follows: PM=Plasma membrane, ER=endoplasmic reticulum, TGN=trans-Golgi network, MVB=multivesicular body, EN=endosome, FC=free cholesterol, FFA=free fatty acid, CYTO CE=re-esterified or esterified non-lysosomal cholesteryl ester (CE), NPC1=site of the Niemann-Pick C1 defect, LAL=lysosomal acid lipase.

Figure 1:
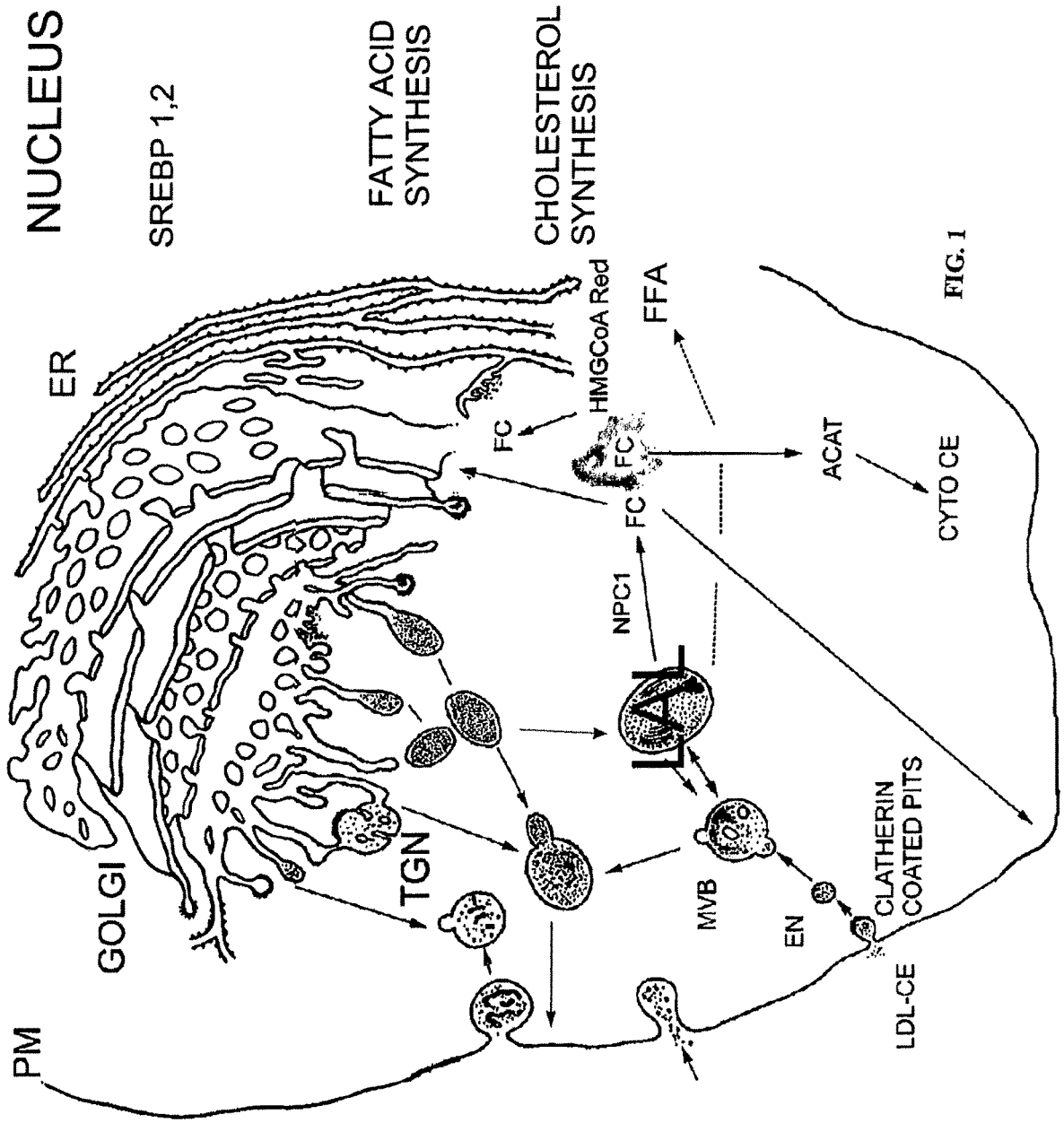
FIG. 1: Schematic of a mammalian cell to illustrate the pathways for cholesterol and fatty acid incorporation into cellular metabolism. Two pathways are illustrated: I) the endogenous synthesis of cholesterol and fatty acids controlled by the SREBP 1 and 2 systems that sense the level of extralysosomal cellular cholesterol as modulated by LAL cleavage of cholesteryl esters and triglycerides in the lysosomes; 2) the exogenous pathway whereby cholesteryl esters and triglycerides enter the cell via receptor mediated endocytosis (shown as LDL-CE as an example) for delivery to the lysosomes inside of the cells. The LDL receptor and several other scavenger receptors participate in this pathway. LAL controls the egress of cholesterol and fatty acids from the lysosomes that enter the cell via this pathway. The liberation of free cholesterol and/or fatty acids by LAL or other such therapeutic compounds leads to a direct effect to reduce cholesterol and FFA synthesis in the cell via the SREBP sensing systems. Reductions in cellular cholesterol and/or FFA can be achieved by this direct effect and/or by removal of the free cholesterol and/or FFA from the cell by transport of cholesterol across the plasma membrane and out of the cell.
Figure 2:
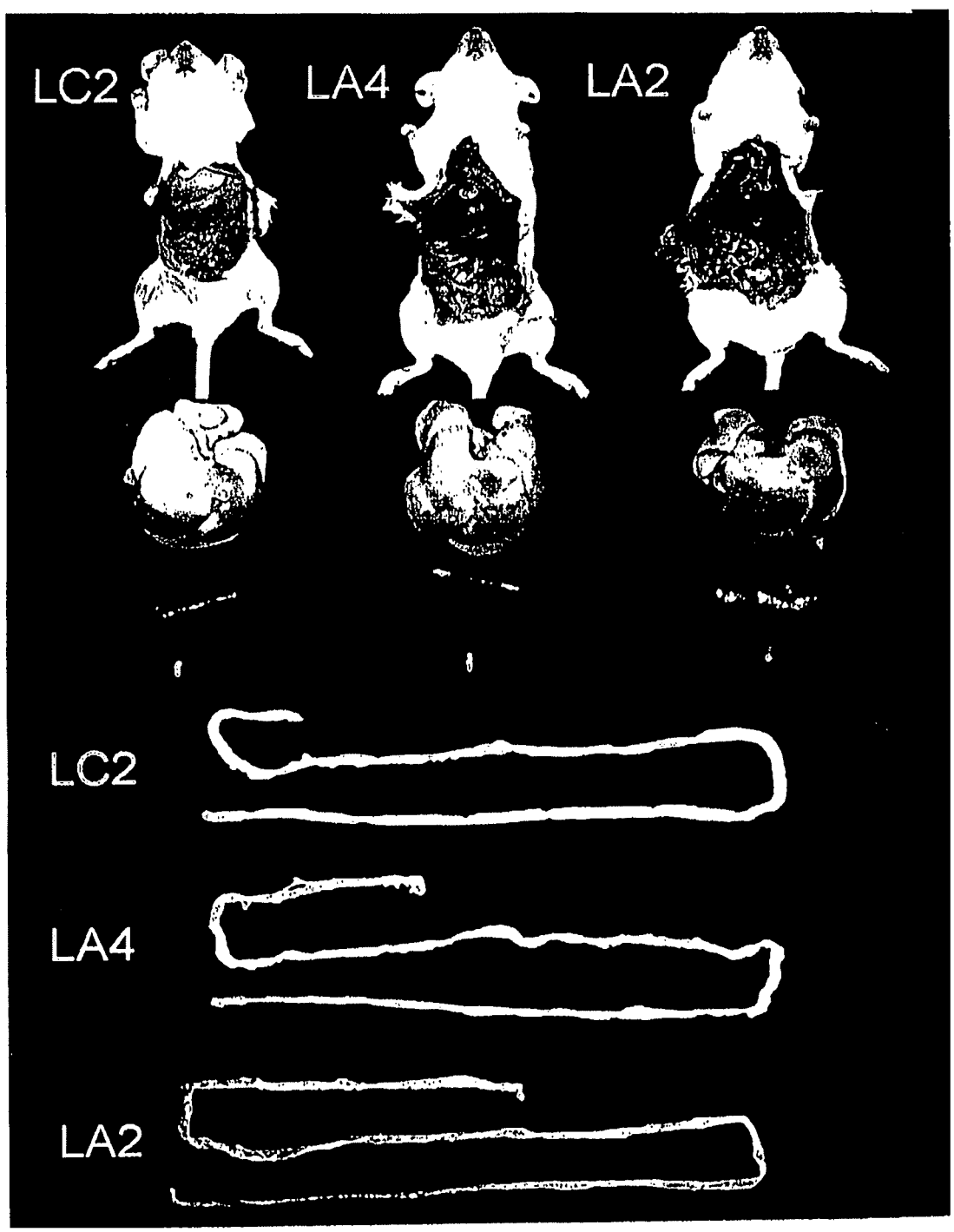

FIG. 2: Typical gross pathology of LAL untreated (LC2) and treated (LA2 and LA4) lal-/- mice: [Top] Ventral views showing the yellow fat-infiltrated lover in a typical (LC2) untreated lal-/- mouse. In treated (LA2 and LA4) lal-/- mice, the livers had essentially normal color. [Middle] Gross appearance of liver (top), spleen (middle) and kidney (bottom) from LC2, LA4 and LA2 mice. The untreated mouse spleen is lighter than that from the treated mice spleens. [Bottom] Gross appearance of the small intestine from untreated LC2 and treated LA4 and LA2 mice. The small intestine of untreated mouse (LC2) gives a lighter appearance, indicating build-up of cholesterol and triglycerides. This is in contrast to the darker intestines shown for the treated mice (LA4 and LA2).

Figure 3:
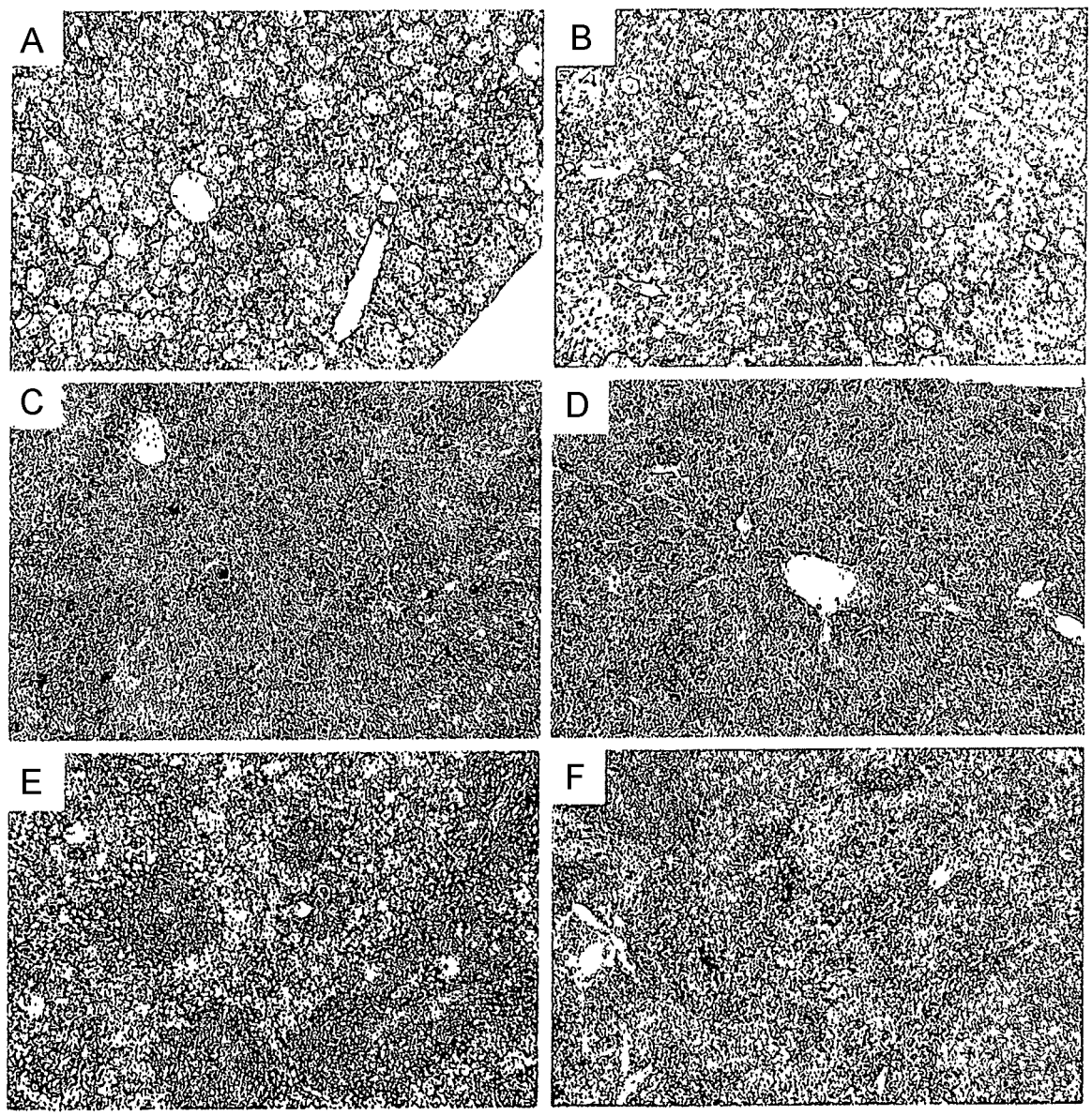

FIG. 3: Light microscopy of the liver, spleen and small intestine from LAL untreated (LC2) and treated (LA2) lal-/- mice. H & E stained sections from liver (panels A and B), spleen (panels E and F). Stained frozen sections from liver (panels C and D). A, C, E, (left) are from untreated lal-/- mice. Panels B, D, and F (right) are from LAL treated mice. Treated mice had substantially diminished macrophage storage cell numbers compared to those in untreated mice. The staining indicates large accumulations of neutral fat in livers from untreated mice and their large decrease to near absence in liver.

Figure 4:
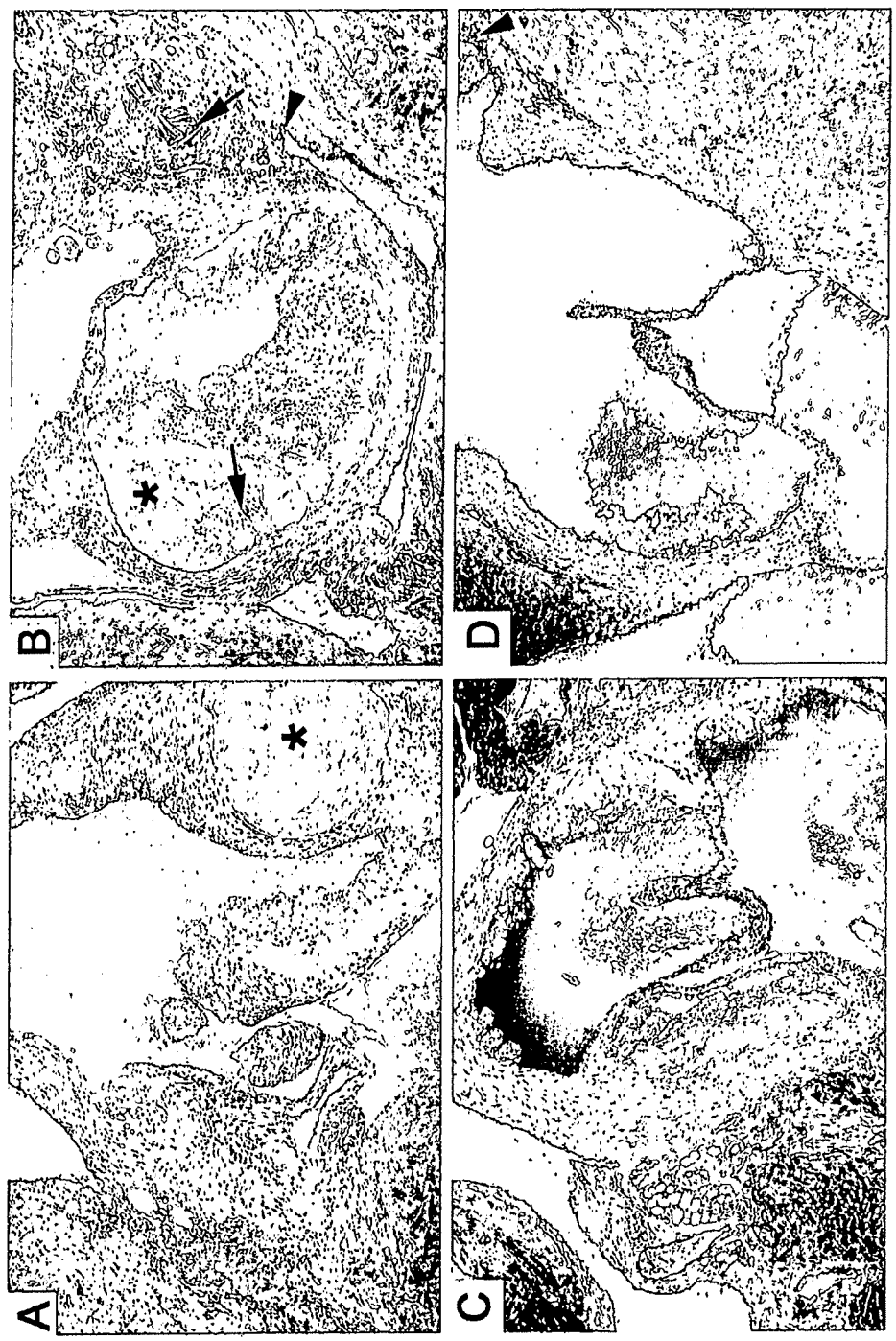

FIG. 4: Representative sections from the aortic valve of ldlr−/− mice with or without LAL treatment stained with H & E. (A nd B) Typical foamy cell-rich fatty streaks in 3.5 month old ldlr−/− mice on HFCD for 2 months. The asterisk indicates a necrotic zone next to disrupted medial layer. The arrows point to cholesterol clefts/crystals. The arrow on the right (cholesterol clefts/crystals) show a coronary artery near the ostium. (C) Reduced foamy cells in the fatty streaks of the aortic valve of the LAL treated mice. This was from the most involved LAL treated mouse. (D) A typical example (3/5) of the normal aortic, valves from LAL treated mice.

DETAILED DESCRIPTION OF THE INVENTION

Definitions

The terms "amino acid" or "amino acid sequence," as used herein, refer to an oligopeptide, peptide, polypeptide, or protein sequence, or a fragment of any of these, and to naturally occurring or synthetic molecules, Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, the term "exogenous lipid hydrolyzing proteins or polypeptides" refers to those produced or manufactured outside of the body and administered to the body; the term "endogenous lipid hydrolyzing proteins or polypeptides" refers to those produced or manufactured inside the body by some type of device (biologic or other) for delivery to within or to other organs in the body.

As used herein, the term "biologically active" refers to a protein having structural, regulatory, or biochemical functions of a naturally occurring molecule.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

The words "insertion" or "addition," as used herein, refer to changes in an amino acid or nucleotide sequence resulting in the addition of one or more amino acid residues or nucleotides, respectively, to the sequence found in the naturally occurring molecule.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, or to any DNA-like or RNA-like material. In this context, "fragments" refers to those nucleic acid sequences which, when translated, would produce polypeptides retaining some functional characteristic, e.g., lipase activity, or structural domain characteristic, of the full-length polypeptide.

The phrases "percent identity" or "percent homology" refers to the percentage of sequence similarity found in homologues of a particular amino acid or nucleic acid sequence when comparing two or more of the amino acid or nucleic acid sequences.

The term "atherosclerosis" refers to the pathologic processes that leads to abnormal accumulation of cholesterol and cholesteryl esters and related lipids in macrophages, smooth muscle cell and other types of cells leading to narrowing and/or occlusion of one or several arteries and arterioles of the body and bodily organs, including but not limited to, the coronary arteries, aorta, renal arteries, corotid arteries, and arteries supplying blood to the limbs and central nervous system. The associated inflammatory reactions and mediators of this pathologic process also are included in this definition.

The term "atherosclerotic plaque" refers to the build up of cholesterol and triglycerides due to atherosclerosis.

Discussion

The consequences of atherosclerosis are a leading cause of mortality and morbidity. Macrophages that accumulate cholesteryl esters are known to be a major component contributing to the build-up of atherosclerotic plaques in coronary arteries as well as the carotid arteries, the aorta and other peripheral vessels throughout the body. These cholesteryl esters are derived from the circulation where they are carried on lipoproteins. The cholesteryl esters enter cells via low-density lipoprotein receptors (LDL-R) and other scavenger receptors for oxidized low-density lipoprotein (LDL) particles. Once internalized, these particles and their attached cholesteryl esters are delivered to the lysosome for cleavage to cholesterol by lysosomal acid lipase (LAL).

Current therapeutic approaches for treating atherosclerosis include dietary manipulation (low cholesterol diets) and exercise, cholesterol synthesis inhibitors and surgical coronary artery by-pass. However, dissatisfaction with the success of these interventions provides the impetus for continued development of new/alternative/adjunctive therapies for this major disease group.

There are two primary methods employed for the treatment of atherosclerosis and the dissolution of atherosclerotic plaque. The first method of treatment is coronary by-pass surgery. This method is used to treat patients with established, unstable angina and/or progressive angina. The second method of treatment is chemical inhibition of hepatic cholesterol synthesis using the class of drugs termed "statins." This approach inhibits the synthesis of cholesterol by inhibiting the action of the rate-limiting enzyme, HMGCoA reductase, in the cholesterol synthetic pathway. Coronary artery by-pass surgery is effective in diminishing angina attacks of selected patients and the statins have been shown to successfully lower plasma cholesterol and diminish the propensity to develop atherosclerotic plaques. However, neither approach offers the potential for direct dissolution of existing atherosclerotic plaques.

LAL represents the major biochemical pathway of cholesteryl ester entry into the body, and is subsequently used to modulate cellular cholesterol biosynthesis. Once LAL liberates cholesterol from cholesteryl esters, the free cholesterol exits the lysosome and leads to the sterol regulatory element binding protein (SREBP) mediated down regulation of cholesterol synthesis. The accumulation of cholesteryl esters within the macrophages of atherosclerotic plaques occurs in the presence of normal amounts of LAL. This fact indicates that the delivery of cholesteryl esters to these cells exceeds the capacity of normal amounts of LAL to catabolite the delivered cholesteryl esters that initiate the development of atherosclerotic plaques. This process disrupts normal cellular metabolism for the regulation of endogenous cellular cholesterol synthesis and leads to excess amounts of cholesterol and cellular cholesteryl ester synthesis via the lack of down regulation of the SREBP-mediated system of cholesterol synthesis and the acyl CoA: cholesterol acyltransferase (ACAT) pathway for intracellular cholesteryl ester synthesis [30].

Similar events occur in the liver, which is the major organ in the body responsible for cholesterol biosynthesis and for maintenance of cholesterol homeostasis. Delivery of LAL to hepatocytes in excess of normal amounts enhances the egress of free cholesterol from the lysosome (i.e., increases the flux of cholesteryl esters through the lysosomal system) that is a major pathway for the metabolism of such lipids delivered to hepatocytes from the portal circulation and the diet. The result is an increase in cholesterol liberated from lysosomes, which subsequently down modulates hepatic cholesterol synthesis and its supply to the body. This diminishes the load of cholesterol and cholesteryl esters to peripheral sites thereby lowering the atherogenic potential.

The use of a suitable protein or polypeptide, such as LAL, or a homologue of LAL possessing similar biological activity, offers an alternative means of therapy for atherosclerosis as well as peripheral vascular disease. LAL functions by preventing the progression or promoting the regression of atherosclerotic plaque legions via two mechanisms: 1) by directly entering the lesional foam cells and enzymatically dissolving the stored cholesteryl esters as well as tri-, di-, and mono-acylglycerides; and 2) by indirectly promoting lysosomal egress of free cholesterol and free fatty acids that could modulate cellular (hepatic, macrophage and other) lipid synthesis mediated by the SREBP or other pathways. Patients who suffer from atherosclerosis have a tendency to have decreased levels of LAL in the atheromatous plaques.

LAL, a member of the lipase family, is a 372 amino acid glycoprotein that is trafficked to the lysosome via the mannose receptor system [31-33]. The cDNA sequence which encodes LAL has been previously reported [34]. This glycoprotein has six glycosylation consensus sequences (Asn-X-Ser-/Thr) and three at $Asn^{15}$, $Asn^{80}$ and $Asn^{252}$ are conserved among members of the lipase gene family. All members of the lipase gene family have conserved GXSXG pentapeptide sequences that contain the active site serine nucleophiles [35-37]. LAL has two such sequences at residues 97-101 and 151-155 with potential serine nucleophiles at residues 99 and 153, where a key nucleophile resides at the Ser 153 residue. LAL cleaves cholesteryl esters and triglycerides in vitro using phospholipid/detergent systems. $Ser^{153}$ has been defined as a part of the Asp-Ser-His catalytic triad common to many lipases.

Suitable lipid hydrolyzing substances for use in this invention include, but are not limited to, glycoproteins such as LAL, homologues of LAL, wherein the homologues possess at least 85% sequence homology, due to degeneracy of the genetic code which encodes for LAL, polypeptides possessing similar biological activity to LAL and non-peptide derived substances. Also included are lipid hydrolyzing proteins and polypeptides which contain the catalytic lipase triad Asp-Ser-His, where the Ser is a $Ser^{153}$ residue. Additional substances include polymorphic variants of LAL in which two of the amino acids are replaced with different amino acids. An example of such polymorphic variants are prepared by cloning LAL from normal human liver cDNA library and changing two nucleotides (C86 to A and G107 to A) which results in substitution of amino acid Pro(-6) to Thr and Gly2 to Arg in LAL, yielding four different polymorphic variants of LAL. Additional amino acid sequences include those capable of lipid hydrolysis, either catalytic or stoichiometric, wherein the residue 153 of the amino acid chain is a serine residue.

Further LAL-derived proteins include those proteins having the native LAL sequence, but which have more than six N-linked acetylglycosylation residues or fewer than six N-linked acetylglycosylation residues. Each glycosylation site has two N-linked acetylglucosamine residues, which are oligosaccharide-terminated, where the oligosaccharide-terminating residue is preferably an α-mannose residue and where there are at least three oligosaccharide-terminating residues at each glycosylation site.

For the treatment of atherosclerosis, the lipid hydrolyzing substance targets receptors which lead to uptake into the lysosome. These receptors include but are not limited to the categories of oligosaccharide recognition receptors, which includes the mannose receptor, the mannose-6-phosphate receptor and the category of peptide sequence recognition receptors, which includes CD 36 and LDL receptors.

Methods of Treatment of Atherosclerosis Using Lipid Hydrolyzing Amino Acid Sequences LAL could be used in conjunction with statins to reduce the level of artherosclerotic plaques. Additionally, LAL could also be used in conjunction with by-pass surgery for some patients who develop restenosis and/or to prevent redevelopment of plaques following surgery. In addition, treatment with therapeutic agents, such as LAL, can effect beneficial improvements in arteries and/or arterioles that cannot be accessed by surgical or other such invasive approaches. Additional advantages of LAL treatment may include the elimination of the need for surgery in some patients and supplying a natural product to patients without the attendant or potential side effects of synthetic chemicals, as is the case for the statin therapy approach.

LAL therapy can also be used for the treatment of two rare human diseases, Wolman Disease and Cholesteryl Ester Storage Disease. Both of these diseases are due to mutations at the LAL locus. The former leads to death in the first year of life and the latter is a prolonged disease with development of cirrhosis of the liver in later life. Neither disease currently has therapy regimes available.

Additional potential therapeutic roles for LAL treatment include its use in the treatment of fatty liver of pregnancy, unspecified fatty infiltration of the liver, peripheral atherosclerotic disease due to secondary diseases such as diabetes mellitus, carotid stenosis due to atherosclerosis, and similar disease states.

The lipid hydrolyzing protein or polypeptide can be used therapeutically either as an exogenous material or as an endogenous material. Exogenous lipid hydrolyzing proteins or polypeptides are those produced or manufactured outside of the body and administered to the body. Endogenous lipid hydrolyzing proteins or polypeptides are those produced or manufactured inside the body by some means (biologic or other) for delivery to within or to other organs in the body. LAL is present in body tissue. Patients who suffer from atherosclerosis have a tendency to have decreased levels of LAL in the atheromatous plaques. In order to achieve such desired results for both direct and indirect treatment of the plaques, the lipid hydrolyzing protein or polypeptide targets specific organs via specific receptors. For example, LAL can target the mannosc receptor systems, or other oligosaccharide specific receptors and enters macrophages, smooth muscle cells, endothelial cells and hepatocytes.

Endogenous Therapy:

An indirect treatment of plaques involves supplying LAL to the major organs of cholesterol biosynthesis, primarily the liver. This leads to a greater net lysosomal throughput of cholesteryl esters and delivery of free cholesterol to the cytoplasm, where overall cholesterol synthesis would be diminished. It also results in a reduction of the endogenous supply of cholesterol from the liver to peripheral organs, i.e. macrophages in developed or developing plaques.

The principles of gene therapy for the production of therapeutic products within the body include the use of delivery vehicles (termed vectors) that can be non-pathogenic viral variants, lipid vesicles (liposomes), carbohydrate and/or other chemical conjugates of nucleotide sequences encoding the therapeutic protein or substance. These vectors are introduced into the body's cells by physical (direct injection), chemical or cellular receptor mediated uptake. Once within the cells, the nucleotide sequences can be made to produce the therapeutic substance within the cellular (episomal) or nuclear (nucleus) environments. Episomes usually produce the desired product for limited periods whereas nuclear incorporated nucleotide sequences can produce the therapeutic product for extended periods including permanently.

Such gene therapy approaches are used to produce therapeutic products for local (i.e., within the cell or organ) or distant beneficial effects. Both may provide decreases in pathologic effects and may combine to produce additive and/or synergistic therapy. For either effect, local or distant, the natural (termed normal) or altered (mutated) nucleotide sequences may be needed to enhance beneficial effects. The latter may be needed for targeted delivery to the specific cellular type involved in the pathology of the disease. For atherosclerosis distant delivery would be needed to macrophages (foam cells), smooth muscle cells and other various cell types within the pathologic lesions, known as atheromata. Subcellular delivery to the lysosomes may also be necessary and variants made available or produced for such an approach.

An approach for the use of lipid removal substances, particularly lipid hydrolyzing proteins and polypeptides for the treatment of atherosclerosis and removal of atherosclerotic plaques, can be achieved by the gene therapy approaches discussed above. Such approaches provide a source of a biologically active human lipid hydrolyzing protein or polypeptide for delivery into the body by biologic or other production systems. This method of introduction can be achieved by internal or production sources (biologic or other, gene therapy vectors, liposomes, gene activation etc.) which lead to the production of biologically active human lipid hydrolyzing proteins and polypeptides by certain cells of the body. The source may provide for the local or distant supply by, for example, direct effects within the cell or by secretion out of the cells for delivery to other cells of the body, like those in atheromatous plaques. This includes, but is not limited to, somatic gene therapy approaches that would allow for the synthesis and/or otherwise production of the therapeutic substance in the body. In particular, nucleotide sequences encoding the functional, lipid hydrolyzing, sequences of the lysosomal acid lipase incorporated into conjugates, liposomes, viral (i.e., lentivirus, adenovirus, adeno-associated virus or other viruses or such virus-like vectors) vectors for expression of the active sequences for therapeutic effect. In addition, nucleotide sequences encompassing the functional components of biologic and therapeutic interest and residing in the body's cells could be made to produce, express or otherwise make the requisite compound in therapeutic amounts. The therapeutic lipid hydrolyzing protein or polypeptide, thus produced in the body, would lead to a reduction or elimination of the atheromatous plaques or other lesions of atherosclerotic plaques.

Variants and homologous nucleotide or encoded sequences of human lysosomal acid lipase incorporated for synthesis and/or production of the active protein/peptide are transiently or permanently integrated into cells for therapeutic production. The normal, polymorphic variants, specifically mutated or modified lysosomal acid lipase sequences may be expressed from the context of the vectors incorporated into cells for normal and/or specifically modified function to enhance or otherwise promote therapeutic effects.

Such sequences can lead to the in vivo synthesis of the desired biologically active human lysosomal acid lipase or other therapeutic proteins within cells after incorporation into cells by various routes as described above. Once within cells, the synthesized biologically active human lysosomal acid lipase or another therapeutic protein hydrolyzes cholesteryl esters and/or triglycerides within the lysosomes following their targeted delivery. The resulting release of free cholesterol from the lysosomes leads to down regulation of the endogenous cholesterol synthetic pathway via the SREBP controlled systems. Additionally, human lysosomal acid lipase or other therapeutic human proteins or polypeptides produced from incorporated nucleotide sequences are secreted from cells, enter the circulatory system and are taken up by distant cells via receptor mediated endocytosis or other such lysosomal delivery systems to the lysosomes of pathologically involved cells of the atheromatous plaques. Such plaques include but are not limited to macrophages and smooth muscle cells. Lysosomal liberation of free cholesterol within such cells has at least two beneficial effects on atheromatous plaque reduction and/or elimination: 1) free cholesterol exits from the lysosome and participates in the SREBP mediated down regulation of endogenous macrophage or other cell type cholesterol synthesis, and 2) free cholesterol exits from the lysosome and exits the cell by reverse cholesterol transport. Both effects are beneficial in reducing the amount of accumulated cholesteryl esters within lysosomes of foam cell macrophages and/or other cells of the atheromatous lesions.

The gene vectors containing the requisite nucleotide sequences or other components necessary for therapeutic expression are introduced into the body's cells by several routes as described above and also their direct introduction into atheromatous plaque cells using delivery by angiographic device.

Endogenous therapy also contemplates the production of a protein or polypeptide where the cell has been transformed with a genetic sequence that turns on the naturally occurring gene encoding the protein, i.e., endogenous gene-activation techniques.

Exogenous Therapy:

A method for the direct treatment of atherosclerotic plaques involves supplying LAL to the plaques and the macrophages, and smooth muscles cells therein, so that the cholesteryl esters and/or triglycerides, which are stored or accumulated within lysosomes of these cells, are degraded and eliminated. This subsequently results in the liberation of cholesterol from the lysosomes and a decrease in endogenous cholesterol synthesis within the foam cells (macrophages and smooth muscles cells). The net effect is to reduce the amount of cholesterol accumulating directly in the target site of pathology and to diminish the size of the plaques and other such legions in situ.

It should be noted that the direct and indirect targeting of the plaques are not mutually exclusive and may be synergistic with both local and global effects on cholesterol homeostasis and the diminution of atherogenic potential.

The lipid hydrolyzing proteins or polypeptides useful in the present invention for exogenous therapy may be administered by any suitable means. One skilled in the art will appreciate that many suitable methods of administering the compound to a host in the context of the present invention, in particular a mammal, are available, and, although more than one route may be used to administer a particular protein or polypeptide, a particular route of administration may provide a more immediate and more effective reaction than another route.

Formulations suitable for administration by inhalation include aerosol formulations placed into pressurized acceptable propellants, such as dichlorodifluoromethane, propane, nitrogen, and the like. The active agent may be aerosolized with suitable excipients. For inhalation administration, the composition can be dissolved or dispersed in liquid form, such as in water or saline, preferably at a concentration at which the composition is fully solubilized and at which a suitable dose can be administered within an inhalable volume.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Formulations suitable for intravenous infusion and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, Higuchi, issued 1973, which is incorporated by reference herein.

The appropriate dosage administered in any given case will, of course, vary depending upon known factors, such as the pharmacodynamic characteristics of the particular protein or polypeptide and its mode and route of administration; the age, general health, metabolism, weight of the recipient and other factors which influence response to the compound; the nature and extent of the atherosclerosis; the kind of concurrent treatment; the frequency of treatment; and the effect desired.

A preferred method of treating mammals possessing atherosclerotic plaque involves introduction of suitable lipid hydrolyzing protein or polypeptide by intravenous infusion of a safe and effective amount of a lipid hydrolyzing protein or polypeptide, so as to cause the diminution and elimination of the plaque. A safe and effective amount of the lipid hydrolyzing protein or polypeptide is defined as an amount, which would cause a decrease in the level of atherosclerotic plaques in a patient while minimizing undesired side effects. An experienced practioner, skilled in this invention would have knowledge of the appropriate dosing ratios. The activity level of the lipid hydrolyzing protein or polypeptide must also be considered in determining the number of units to administer to achieve the desired effect. Thus, the activity level of the lipid hydrolyzing protein or polypeptide should be sufficient to cause a reduction in atherosclerotic plaques within a reasonable dosage administered.

Experimental Examples

Study Design

This study was designed for age-matched cohorts of lysosomal acid lipase deficient, lal−/− or low density lipoprotein receptor deficient, ldlr−/−, mice as an open-label, controlled trial of treated and untreated mice. A single dose of LAL was used in all mice. All mice were sacrificed after 30 days of LAL administration. LAL was given as an i.v. bolus via tail vein every third day for 30 days. The cohorts were divided into equal groups for injections on alternate days. Injections were begun at 2.0 or 2.5 months of age for the lal−/− or ldlr−/− mice, respectively. The overall study design is presented in Table 1. The lal−/− mice received a regular chow diet throughout the entire study period. LAL dosing was begun at 2 months of age. The ldlr−/− mice were maintained on a regular chow diet for 1.5 months and then placed on a high cholesterol diet (7.5% fat; 1.25% cholesterol). The LAL dosing was started after the ldlr/1− mice had been on the high fat/high cholesterol diet for 30 days; i.e., at 2.5 months of age. Doses of LAL in the treated groups were 1.48 U (21 µg; 70 µl) LAL in 1× PBS with 2% human serum albumin and 10 mM of dithiothreitol (MT). The control groups received 1× PBS with 2% HSA and 10 mM of DTT. The final cohort was the lal−/−; ldlr−/− combined deficiency.

The mice avidly consumed the high fat/high cholesterol diet and tolerated the injections well. All injections (325) were successful with i.v. administration obtained for all. One ldlr−/− mouse died just prior to initiating the injections. The high mortality in the lal−/−; ldlr-1− mice was due to massive small bowel infarction possibly secondary to vessel blockage from massive macrophage infiltration of the submucosa and lamina propria. The data from these latter double homozygotes: arc not included here.

Samples for plasma lipid determinations and antibody analyses were obtained at 32 days after the first injection. All mice were sacrificed 48 h after the final LAL injection.

TABLE 1

Study Design

| Name | Genotype | Diet | # of mice | Age* (mos.) | Injection | Dosage*** (U) | Total Injections |
|---|---|---|---|---|---|---|---|
| LC | lal-/- | chow | 5 | 2 | PBS** | 0 | 10 |
| LA, LB | lal-/- | chow | 8 | 2 | LAL | 1.48 | 10 |
| RC | ldlr-/- | HF/HCh | 4 | 2.5 | PBS | 0 | 10 |
| RA, RB | ldlr-/- | HF/HCh | 8 | 2.5 | LAL | 1.48 | 10 |
| LRC | lal-/-/ldlr-/- | HF/HCh | 4 | 2.5 | PBS | 0 | 10 |
| LRA, LRB | lal-/-/ldlr-/- | HF/HCh | 8 | 2.5 | LAL | 1.48 | 10 |

*The age refers to that at beginning of injections.
**The control injection was 1 × PBS, with 2% HSA and 10 mM DTT.
***Doses were given every third day to each mouse. 1.48U = 21 μg.

Stability of LAL Activity

The stability of LAL activity at 4° C. was monitored every 3-4 days for 34 days. The LAL activities remained relatively stable over this period of time, although rigorous standardization of the assay remains to be accomplished.

General Methods

Animals. The mice were provided care in accordance with institutional guidelines and all procedures received prior approval by the IACUC at the Children's Hospital Research Foundation, Cincinnati, Ohio. The lal-A mice originated from mixed genetic backgrounds of 129Sv and CF-1. The ldlr−/− mice were purchased from Jackson Laboratory and were cohorts of C57BL6/J. Mice were housed in microisolation, under 12 h/12 h, dark/light cycles. Water and food, regular chow diets or HFCD, were available ad libitum. The mice were genotyped by PCR-based screening of tail DNA.

Plasma lipid analyses. Blood was collected from the inferior vena cava (IVC) of mice after they had been anesthetized with 200 μl triple sedative (Ketamine, Acepromazine, and Xylazine). Plasma was collected after centrifugation (5,000×g; 10 min; 4° C.) of blood and stored at −20° C. Total plasma free cholesterol was determined colorimetrically with a COD-PAP kit (Wako Chemicals). Total plasma, triglycerides were determined in plasma samples with a Triglycerides/GB kit (Boehringer Mannheim). Total plasma cholesterol was determined using a Cholesterol/HP kit (Boehringer Mannheim).

Tissue Lipid analyses. Total lipids were extracted from liver, spleen and small intestine by the Folch method (Folch, J., Lees. M., and Sloane-Stanley, G. H. (1957) A simple method for the isolation and purification of total lipids from animal tissue. *J. Biol. Chem.*, 226, 497-505). Triglyceride concentrations were measured using chemical analysis developed by Biggs. Briefly, both standards and samples in chloroform were evaporated under vacuum. The lipids were resuspended into the following reagents in order: 0.5 ml of isopropanol, 4.5 ml of $H_2O$:isopropanol:40 mM $H_2SO_4$ (0.5:3.0:1.0) and 2.0 ml of Heptane, and mixed by vigorous agitation at each step. The tubes were left to biphase 5 minutes). In a set of new tubes, 80 mg of florisil was added and 1.0 ml of the upper phase from each sample was transferred into tubes that contained florisil and mixed by agitation. Then, 0.2 ml of this upper phase was transferred to a new set of tubes and 28 mM sodium alkoxide (2.0 ml) was added and mixed carefully. The tubes were incubated at 60° C. for 5 min. Sodium metaperiodate (3 mM, 1 ml) was added to each tube and mixed well. The tubes were left to oxidize for 45 minutes. Finally, 1.0 ml of 73 mM acetyl acetone was added to each tube and incubated at 60° C. for 20 min. The tubes were cooled at room temperature (~25 min), read at 410 nm on a Beckman DU640 spectrophotometer.

Total tissue cholesterol concentrations were measured using the O-phthalaldehyde. Briefly, cholesterol standards and Folch extracted samples were evaporated under $N_2$. O-phthalaldehyde (3 ml, Sigma) was added to each cholesterol standard and tissue sample and mixed. Concentrated sulfuric acid (1.5 ml) was added slowly and, then, mixed and cooled for 5-10 min, and read at 550 nm in a Beckman DU640 spectrophotometer.

Western blot analysis and LAL activity assay: Immunoblots were conducted with anti-LAL antiserum as described. LAL activities were estimated with the fluorogenic substrate, 4-MU-oleate (4-MUO). All assays were conducted in duplicate. Assays were linear within the time frame used and less than 10% of substrates were cleaved.

Histological Analyses. Light microscopic examinations of the livers, spleen, intestine, adrenal glands, kidneys, heart, lung, thymus, pancreas, and brain were performed. The sections were stained with hematoxylin/eosin (paraffin embedded) or Oil red-O (ORO) (frozen sections) for light microscopic analysis.

Immunohistochemical staining. Immunohistochemical analyses were with paraffin-embedded liver sections and were performed with rabbit anti-LAL antibody. The endogenous peroxidase activity was saturated by incubation in methanol containing 0.5% $H_2O_2$ for 10 min.

The primary antibody (1:200) was incubated at 40° C. for overnight. The sections were then washed with 1× PBS three times (5 min per wash), incubated with alkaline phosphatase-conjugated IgG as secondary antibody for 30 min at room temperature, and washed with 1× PBS for 5 min. The signal was detected using VECTASTAIN ABC-AP kit (Vector) and counter stained with Nuclear Fast Red.

LAL uptake studies in J774E and J774A. I macrophage cultures: J774E and J774A.1 cells were maintained in DMEM medium with 60 μM of 6-Thioguanine or in DMEM medium, respectively, supplemented with 10% fetal calf serum, penicillin and streptomycin (37° C.; 5% $CO_2$). For the uptake studies, cells were seeded at $2\times10^5$ per well one day before adding LAL or Ceredase. At designated post-incubation times, cells were washed with 1× PBS twice, collected with a rubber policeman, and centrifuged (12,000 rpm, 1 min.) at room temperature. The intracellular proteins were extracted by cell lysis with 1% taurocholate/1% Triton X-100, frozen/thawed five times (dry ice and 37° C. water bath), and centrifuged (12,000 rpm, 10 min.) at 4° C. The protein extracts were analyzed by Western blot.

For immunofluorescence staining, cells ($1.5\times10^5$) were seeded on chamber slide, incubated with LAL, for 5, 18 or 24 hrs, washed with PBS twice, and fixed with 2% Paraformaldehyde for 1 hr. Immunofluoresence staining was performed.

Results

1) Reduction of lipid storage in liver, spleen, and small intestine of lal−/− mice following LAL treatment.

a. Phenotypic and Gross Pathologic Changes (FIG. 2): In lal−/− mice, treatment with LAL resulted in significant correction of lipid storage phenotypes in various organs. At 3 months of age, untreated lal−/− mice developed a yellow/white creamy color to the liver and significant hepatosplenomegaly was present. In comparison, the LAL treated mice had livers and spleens with much more normal colors. The normal livers in age matched controls were about 5% of body weight whereas the livers were 14% in the untreated lal−/− mice. LAL administration decreased this by about 30% (p=0.0029). The splenic weights were similar in the untreated and treated lal−/− mice (p=0.5044). However, the color of the spleen reverted to near normal in the treated group. The small intestine in untreated lal−/− mice was yellow in the duodenum and creamy white in the jejunum. In the treated group, the small intestine partially reverted to a normal color.

b. Histologic Evaluation: H & E or Oil-Red-O staining of liver, spleen and small intestine from untreated and treated mice showed clear differences. In liver, the LAL treated lal−/− mice had reductions in the size and number of lipid filled Kupffer cells (see FIGS. 3A and B). Hepatocytes have less lipid storage than Kupffer cells in untreated mice and this hepatocyte storage appeared unchanged in the treated group. Using Oil-Red-O staining for neutral lipids, a significant difference between the livers of the treated and untreated mice was apparent (see FIGS. 3C and D). In the spleen, the treated group showed a reduction in lipid storage cells compared to those present in untreated mice. In the small intestine, the Oil-Red-O staining of LAL treated and untreated mice showed substantial differences. The sections of intestine from untreated mice were full of Oil-Red-O staining cells (macrophages) in lamina propria while comparable sections from treated mice were almost completely negative for Oil-Red-O staining. The aortic arches, aortic base and valves, and coronary arteries of lal−/− mice, treated or untreated, were essentially normal throughout the study.

c. Immunohistochemistry: Immunohistologic analyses of liver with anti-LAL (*E. coli* produced recombinant hLAL) showed predominantly dark staining (positive) of the sinusoidal lining cells. Some antigen could be detected in the storage cells, but this signal was at a low level due to the very large dilution space presented by these cells. The samples of liver were obtained 30 min. after injection. The uninjected lal−/− mice had undetectable lal.

d. Biochemical Findings: Tissue cholesterol (both free and esterified) and triglycerides from liver, spleen and small intestine were determined by chemical analyses. Compared to age matched wild-type mice, the lal−/− mice have elevated cholesteryl esters and triglycerides in several tissues. The average total cholesteryl ester per organ at 3.5 months of age was increased 31-fold in liver and 19-fold in spleen compared to wild-type. LAL administration to such mice was associated with reductions of total cholesterol by 47% in total liver (267.22±8.22 mg vs. 144.23±7.99 mg; p=0.0003, n=3) and by 69% in total spleen (8.73±0.43 mg vs. 2.63±0.50 mg, p=0.0008, n=3). Similar decreases of triglycerides also were observed: 58% in total liver (26.52±17.93 mg vs. 39.79±6.38 mg, p=0.047, n=4) and 45% in total spleen (8.23±0.68 mg vs. 4.55±1.26 mg, p=0.042, n=4). Although no change in the concentration of cholesterol in small intestine was observed (p=0.67), the triglyceride concentration of the treated group was 65% reduced (49.52±2.40 μg/mg vs. 17.09±4.8 μg/mg, p=0.042, n=4).

e. Summary

Limited treatment of lal−/− mice with LAL (10 injections in 30 days, 1.48 U/dose) led to gross, histologic and biochemical corrections of cholesterol and triglyceride levels in treated mice.

2. Plasma chemistries and lipid levels in lal−/− and ldlr−/− mice.

No differences in plasma glucose levels were observed in treated or untreated lal−/− or ldlr−/− mice although ldlr−/− mice have higher plasma glucose levels than wild type or lal−/− mice. The lal−/− and ldlr−/− mice had increased plasma non-esterified fatty acids (NEFA) levels compared to the wild-type controls (162% and 227%, respectively). LAL administration was associated with increases of the NEFA by 32.6% in lal−/− mice and 24.5% in ldlr−/− mice. Plasma triglycerides levels decreased in treated lal−/− mice, but were unchanged in ldlr−/− mice. The HFCD produced hypercholesterolemia in ldlr−/− mice. The plasma free cholesterol concentration increased 22-fold and plasma cholesteryl ester concentration increased 13.8-fold compared to wild-type mice. The LAL treated ldlr−/− mice had decreases in plasma free cholesterol of 18.2% (p=0.0894) and in cholesteryl esters of 26.7% (P=0.0025). The free cholesterol and cholesterol ester levels were unchanged in treated lal−/− mice.

3. Histologic and Biochemical Effects of LAL Administration in ldlr−/− mice.

a. Gross Anatomic and Histologic Studies

The visceral organs of these mice appeared normal. Whole mounts of the aortic arches were prepared from ldlr−/− mice and examined by transillumination. At 3.5 months, all (3/3) untreated ldlr−/− mice had extensive lesions of the arch and take-offs of the major vessels, i.e., brachiocephalic arteries. Although not quantitatively determined, LAL administration appeared to have little effect on these lesions in treated ldlr−/− mice.

To evaluate the coronary artery lesions, the hearts of treated and untreated ldlr−/− mice were sequentially sectioned and analyzed. Four ldlr−/− mice were untreated. One of these was found dead just before the LAL administration began (at age of 2.5 months). Eight mice received LAL and all survived for the entire study period. The results are summarized in Table 2. All untreated ldlr−/− mice had severe plaque lesions in aortic valve and ostia of the coronary arteries (see FIGS. 4A and B). Of the aortic valves examined in the treated group, two had mild to moderate (++), one had very mild (+), and two had no accumulation of foam cells (see FIG. 4C). The aortic valves from three treated mice were not examined histologically since they had been removed for the whole mount aortic arch studies.

The coronary lesions in the untreated group were extensive and multifocal. All had heavy infiltration of the coronary ostia by macrophages with plaques extending a considerable distance in the coronary arteries. Also, individual isolated and scattered plaques were found throughout the first third of the coronary arteries. In one case, the main branch of the left coronary was completely obliterated with an advanced lesion containing cholesterol crystals and apparent inflammatory. In comparison, 7/8 of the treated ldlr−/− mice had normal coronary vessels (see Table 2). One LAL treated ldlr−/− mouse had foamy cells in one small intramuscular coronary vessel. The other coronary arteries in this mouse were normal. This particular mouse (RAI) also had mild-moderate lesions of the aortic valve.

To obtain a more quantitative assessment of the coronary artery lesions in ldlr−/− mice, sequential H&E sections (total=210; 10 μm) of the heart were examined in an untreated mouse (RC2) and in one treated mouse (RB2). RC2 had multiple plaques in coronary arteries whereas RB2 had completely normal coronary arteries.

TABLE 2

Effect of LAL on the Aortic Valves and Coronary Arteries of ldlr-/- Mice

| Designation | Aortic Valve Lesion | Coronary Artery Lesions |
|---|---|---|
| LAL Untreated Mice | | |
| RC2 | ++++ | ++++ |
| RC3 | ++++ | +++ |
| RC4 | ++++ | ++++ |
| LAL Treated Mice | | |
| RA1 | ++ | + |
| RA2 | + | - |
| RA3 | + | - |
| RA4 | ++ | - |
| RB1 | - | - |
| RB2 | - | - |
| RB3 | ND | - |
| RB4 | ND | - |

++++ = severe lesions; +++ = moderate, ++ = mild-moderate; + = mild; - = no lesions; ND = Not done due to aortic arch removal for whole mounts.

These results show a major selective effect of a single fixed dose level of LAL on the presence of aortic valvular and coronary artery foam cell and progressive atherogenic lesions.

b. Biochemical Studies:

Plasma lipid results are reported above for the ldlr-/- treated and untreated groups. Liver and splenic cholesterol and triglyceride levels were increased over wild-type mice in the untreated ldlr-/- group. No significant effects were observed on the total cholesterol in liver (p=0.8816) and spleen (p=0.1061), or cholesterol concentration (0.0927) in the small intestine. The triglycerides were reduced 65.1% in total liver (91.54±1.98 mg vs. 59.60±6.86 mg; p=0.002), and 53.3% in total spleen (3.24±0.39 mg vs. 1.73±0.33 mg; p=0.0183). The concentration of triglycerides in small intestine also was reduced 43% (41.74±3.69 mg/mg vs. 23.79±2.08 µg/mg p=0.001).

c. Antibody Studies:

Serum was obtained at sacrifice from each mouse of each genotype and used in Western analyses. Prep #3 (2.65 ng/well) was used as antigen. Serum was used at 1:100 dilutions. All mice exposed to 10 injections of LAL gave positive western signals. The positive bands co-migrated with the LAL detected with rabbit anti-LAL. With one mouse serum positive signals were achieved with 1:100 to 1:6400 dilutions using Prep #3. Additional studies were conducted to determine the reactivity of these mouse sera to LAL or unglycosylated LAL produced in E. coli. Using 2.65 ng of antigen, the unglycosylated LAL gave very low to absent signals with all but one mouse serum. These results indicate that the antibody's specificity is directed more toward the oligosaccharides than the LAL protein in these conformations.

Summary of Data

The data from the ldlr-/- data show clear and dramatic effects of LAL administration on the presence of aortic valvular and coronary artery plaques and foam cells. All of the lesions were greatly diminished or absent in the treated mice compared to very severe lesions in the untreated cohort. The changes in hepatic, splenic and intestinal triglycerides indicate a direct effect of the LAL in these organs.

REFERENCES

1) Du, H.; Witte, D. F.; Grabowski, G. A. 1996, *Journal of Lipid Research*, vol. 37, pp. 937-949.
2) Hun, X., Yokoyama, C., Wu, J., Briggs, M. R., Brown, M. S., Goldstein, J. L., and Wang, X. 1993, *Proc. Natl. Acad. Sci.*, vol. 90, pp. 11603-11607.
3) Brown, M. S. and Goldstein, J. L. 1997, *Cell*, vol. 89, pp. 331-340.
4) Goldstein, J. L. and Brown, M. S. 1990, *Nature*, vol. 343, pp. 425-430.
5) Wang, X., Sato, R., Brown, M. S., Hua, X., and Goldstein, J. L. 1994, *Cell*, vol. 77, pp. 53-62.
6) Goldstein, J. L., Basu, S., and Brown, M. S. 1983, *Met. in. Enzymology*, vol. 8, pp. 241-260.
7) Goldstein, J. L., Dana, S. E., Faust, J. R., Beaudet, A. L., and Brown, M. S. 1975, *J. Biol. Chem*, vol. 250, pp. 8487-8495.
8) Kim, J. B. and Spiegelman, B. M. 1996, *Genes. Dev.* vol. 10, pp. 1096-1107.
9) Ericsson, J., Jackson, S. M., Lee, B. C., and Edwards, P. A. 1996, *Proc. Natl. Acad. Sci. USA* vol. 93, pp. 945-950.
10) Du, H., Witte, D. P., and Grabowski, G. A. 1996, *J. Lipid Res.* vol. 37, pp. 937-949.
11) Osborne, T. F. and Rosenfeld, J. M. 1998, *Curr. Opin. Lipidol.* vol. 9, pp. 137-140.
12) Sakai, J., Duncan, B. A., Rawson, R. B., Hua, X., Brown, M. S., and Goldstein, J. L. 1996, *Cell*, vol. 85, pp. 1037-1046.
13) Sakai, J., Nohturfft, A., Cheng, D., Ho, Y. K., Brown, M. S., and Goldstein, J. L. 1997, *J. Bio. Chem.*, vol. 272, pp. 20213-20221.
14) Yokoyama, C., Wang, X., Briggs, M. R., Admon, A., Wu, J., Hua, X., Goldstein, J. L., and Brown, M. S. 1993, *Cell*, vol. 75, pp. 187-197.
15) Hua, X., Wu, J., Goldstein, U., Brown, M. S., and Hobbs, H. H. 1995, *Genomics*, vol. 25, pp. 667-673.
16) Sato, R., Yang, J., Wang, X., Evans, M. J., Ho, Y. K., Goldstein, J. L., and Brown, M. S. 1994, *J. Biol. Chem.*, vol. 269, pp. 17267-17273.
17) Sakai, J., Nohturtft, A., Cheng, D., Ho, Y. K., Brown, M. S., and Goldstein, J. L. 1997, *J. Bio. Chem.* vol. 272, pp. 20213-20221.
18) Fielding, C. J. and Fielding, P. E. 1997, *J. Lipid. Res.* vol. 38, pp. 1503-1521.
19) Dietschy, J. M. 1990, *Hospital Practice*, pp. 67-78.
20) Rigotti, A., Trigatti, B. L., Penman, M., Rayburn, H., Herz, J., and Krieger, M. 1997, *Proc. Natl. Acad. Sci. USA*, vol. 94, pp. 12610-12615.
21) Temel, R. E., Trigatti, B., DeMattos, R. B., Azhar, S., Krieger, M., and Williams, D. L. 1997, *Proc. Natl. Acad. Sci. USA*, vol. 94, pp. 13600-13605.
22) Jian, B., Llera-Moyer, M., Ji, Y., Wang, N., Phillips, M. C., Swaney, J. B., Tall, A. R., and Rothblat, G. H. 1998, *J. Bio. Chem.*, vol. 273, pp. 5599-5606.
23) Johnson, M. S. C., Svensson, P. A., Helou, K., Billig, H., Levan, G., Carlsson, L. M. S., and Carlsson, B. 1998, *Endocrinology*, vol. 139, pp. 72-80.
24) Fluiter, K., Westhuijzen, D. R., and Berkel, T. J. C. 1998, *J. Bio. Chem.*, vol. 273, pp. 8434-8438.
25) Id. at 21.
26) Id. at 22.
27) Somerharju, P. and Lusa, S. 1998, *Biochem. Biophy. Acta.*, vol. 1389, pp. 112-122.
28) Assman, G. and Seedorf, U. 1995, *The Metabolic and Molecular Bases of Inherited* Disease, pp. 2563-2587.
29) Sheriff, S. and Du, H. 1995, *Am. J. Hum. Genet.*, vol. 57, page 1017A.
30) Sheriff, S., Du, H., Grabowski, G. A. 1995, *J. Biol. Chem.*, vol. 270, pp. 27766-27772.

31) Amies, D., Merkel, M., Eckerskorn, C., Greten, H. 1994, *Eur. J. Biochem.*, vol. 219, pp. 905-914.
32) Neufeld, E. F., Sando, G. N., Garvin, A. J., Rowl, W. 1977, *J. Supramol. Struct.*, vol. 6, pp. 95-101.
33) Sando, G. N., Henke, V. L. 1982, *J. Lipid Res.*, vol. 23, pp. 114-123.
34) Anderson, R. A., and Sando, G. N. 1991, *J. Biol. Chem.*, vol. 266, pp. 22479-22484.
35) Komaromy, M. C., Schotz, M. C. 1987, *Proc. Natl. Acad. Sci. USA*, vol. 84, pp. 1526-1530.
36) Lowe, M. E., Rosenblum, J. L. 1989, *J. Biol. Chem.*, vol. 264, pp. 20042-20048.
37) Shimida, Y., Sugihara, A., Tominaga, Y., Tsunaawu, S. 1989, *J. Biochem. (Tokyo)*, vol. 106, pp. 383-388.

What is claimed is:

1. A sterile, aqueous solution consisting of
a) human lysosomal acid lipase (hLAL) protein;
b) human serum albumin;
c) one or more buffers; and
d) water.

2. A sealed ampule containing the composition of claim 1.

3. A sealed vial containing the composition of claim 1.

* * * * *